United States Patent [19]

Mizukami et al.

[11] Patent Number: 5,364,560
[45] Date of Patent: Nov. 15, 1994

[54] LIQUID CRYSTAL COMPOUND AND LIQUID CRYSTAL DISPLAY DEVICE

[75] Inventors: Masamichi Mizukami, Tsukuba; Tomoyuki Yui, Nagareyama; Masahiro Johno, Tsukuba; Yoshihisa Arai, Tsukuba; Hiroshi Mineta, Tsukuba, all of Japan

[73] Assignee: Mitsubishi Gas Chemical Co., Inc., Tokyo, Japan

[21] Appl. No.: 827,631

[22] Filed: Jan. 29, 1992

[30] Foreign Application Priority Data

Jan. 30, 1991 [JP] Japan .................................. 3-027649
Feb. 28, 1991 [JP] Japan .................................. 3-055737
Apr. 25, 1991 [JP] Japan .................................. 3-122633

[51] Int. Cl.$^5$ .................. C09K 19/12; C07C 69/76; C07C 43/02; G02F 1/13
[52] U.S. Cl. ..................... 252/299.65; 252/299.01; 560/59; 560/61; 560/62; 560/65; 560/73; 560/76; 560/83; 560/102; 568/631; 568/647; 568/661; 359/103
[58] Field of Search .......... 252/299.01, 299.64, 252/299.65, 299.66, 299.67; 560/59, 61, 62, 65, 73, 76, 102, 83; 568/631, 647, 661; 359/103

[56] References Cited

U.S. PATENT DOCUMENTS

| | | | |
|---|---|---|---|
| 4,921,632 | 1/1990 | Nakamura | 252/299.1 |
| 5,167,861 | 12/1992 | Suzuki et al. | 252/299.65 |
| 5,194,179 | 3/1993 | Suzuki et al. | 252/299.66 |
| 5,262,086 | 11/1993 | Suzuki et al. | 252/299.65 |
| 5,264,150 | 11/1993 | Yui et al. | 252/299.64 |

FOREIGN PATENT DOCUMENTS

| | | |
|---|---|---|
| 0188222 | 7/1986 | European Pat. Off. |
| 0197677 | 10/1986 | European Pat. Off. |
| 0251335 | 1/1988 | European Pat. Off. |
| 0327349 | 8/1989 | European Pat. Off. |
| 0330491 | 8/1989 | European Pat. Off. |
| 0350330 | 1/1990 | European Pat. Off. |
| 0350937 | 1/1990 | European Pat. Off. |
| 01213390 | 8/1989 | Japan . |

OTHER PUBLICATIONS

Chem. Abstracts, vol. 109, No. 14, 3 Oct. 1988, Columbus, Ohio, US; abstract No. 119862, p. 657; & JP-A-63 027 590 (Dainippon Ink and Chemicals, Inc.).
Chem. Abstracts, vol. 111, No. 4, 24 Jul. 1989, Columbus, Ohio, US; abstract No. 31748, p. 561; & JP-A-63 307 837 (Daicel Chemical Industries, Ltd.).
Database WPIL Sec. Ch, Wk. 8940, Derwent Publications, Ltd., London, GB; Class E, AN 89-289849 & JP-A-1 213 390 (Chisso Corp.) 28 Aug. 1989.

*Primary Examiner*—Shean Wu
*Attorney, Agent, or Firm*—Sherman and Shalloway

[57] ABSTRACT

An antiferroelectric liquid crystal compound which is a compound represented by

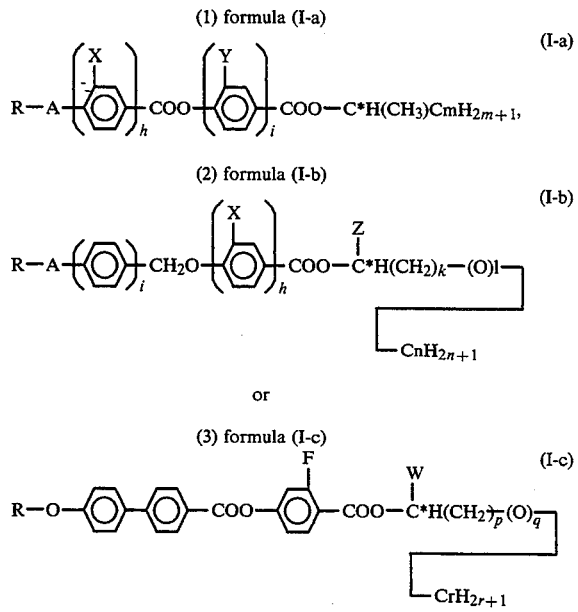

wherein R denotes a linear aliphatic alkyl group having 6 to 14 carbon atoms; A denotes a single bond or an oxygen atom; X and Y independently denote a hydro- (Abstract continued on next page.)

gen atom or a fluorine atom but they are not hydrogen atoms at the same time; h and i are independently 1 or 2; m is an integer of 3 to 10; Z denotes $CH_3$, $C_2H_5$ or $CF_3$; k is 0 or an integer of 5 to 8; l is 0 or 1; n is an integer of 1 to 6; W denotes $CH_3$ or $CF_3$; when W is $CH_3$, p and q are both 0 and r is 8; when W is $CF_3$, p is 5 to 8, q is 1 and r is 1 to 4; and C* denotes an asymmetric carbon atom, and a liquid crystal display device using same.

12 Claims, 24 Drawing Sheets

LIQUID CRYSTAL COMPOUND AND LIQUID CRYSTAL DISPLAY DEVICE

DETAILED DESCRIPTION OF THE INVENTION

This invention relates to a novel liquid crystal compound and a liquid crystal display device. More specifically, this invention relates to a novel antiferroelectric phenyl ester-type liquid crystal compound and a liquid crystal display device using same.

PRIOR ART

Liquid crystal display devices have been to date used as various small-screen devices because a voltage is low, an electric power consumption is low and thin display is possible. Since the liquid crystal display devices have, however, recently found use in the fields of information, office automation appliances, television, etc., high-performance, large-sized liquid crystal display devices having higher resolution and higher display qualities than the ordinary CRT display devices have been increasingly demanded rapidly.

Nevertheless, so far as the present nematic liquid crystals are used as display devices, even active matrix liquid crystal display devices employed in liquid crystal television sets have difficulty to produce a large screen with low cost owing to intricacy of their production process and their low yields. Meanwhile, simple matrix STN liquid crystal display devices are not necessarily easy to drive the large screen with high quality, and the response time is also limited. Under the circumstances, at the present stage, the nematic liquid crystal display devices cannot be said to meet the demand for the high-performance, large-sized liquid crystal display devices.

PROBLEMS THE INVENTION AIMS TO SOLVE

On the other hand, liquid crystal display devices using ferroelectric liquid crystal compounds arouse interest as liquid crystal display devices having high-speed response. Surface stabilized ferroelectric liquid crystal (SSFLC) devices reported by N. A. Clark and S. T. Lagerwall are noteworthy in that they have high-speed response and a wide viewing angle that have not ever been provided as well as memory effect [N. A. Clark and S. T. Lagerwall, Appl. Phys. Lett. 36(1980) 899].

Switching characteristics of said SSFLC devices have been studied in detail, and many ferroelectric liquid crystal compounds have been proposed to optimize various properties.

Said SSFLC, however, suffer serious problems that since threshold characteristics are not sufficient, contrast is poor, high-speed response is not realized, stable memory effect is hardly realized, alignment is destroyed by mechanical shock and is hardly recovered, and so forth.

Separately, devices of switching mechanism different from SSFLC devices have been also developed at the same time. Tristable switching of liquid crystal compounds having an antiferroelectric phase (hereinafter referred to as "antiferroelectric liquid crystal compounds") are one of the new switching mechanisms (Japanese Journal of Applied Physics, vol. 27, No.5, p. L729, 1988).

Antiferroelectric liquid crystal devices (devices using antiferroelectric liquid crystal compounds) have three stable states, i.e., two uniform states (Ur, Ul) observed in the ferroelectric liquid crystal devices and a third state. The third state is an antiferroelectric phase reported by Chandani, et al (Japanese Journal of Applied Physics, vol. 28, p. L1261, 1989 and Japanese Journal of Applied Physics, vol. 28, p. L1265, 1989).

Such tristable switching is the first characteristic feature of the antiferroelectric liquid crystal devices. The second characteristic feature of the antiferroelectric liquid crystal devices is a sharp threshold against an applied voltage. The third characteristic feature thereof is memory effect. Liquid crystal display devices having high-speed response and good contrast can be realized by utilizing these excellent characteristic features.

Another great characteristic feature is that a layer structure is easily switched by an electric field (Japanese Journal of Applied Physics, vol. 28, p. L119, 1989, and Japanese Journal of Applied Physics, vol. 29, p. L111, 1990). As a result, it becomes possible to realize less defective liquid crystal display devices having an alignment self-recovering ability.

As the antiferroelectric liquid crystal compound, those described in Japanese Laid-open Patent Appln. (Kokai) Nos. 213390/1989, 316339/1989, 316367/1989, 316372/1989 and 28128/1990 and Liquid Crystals, vol. 6, No. 2, p. 167, 1989 are known. Meanwhile, studies over the antiferroelectric liquid crystal compounds have just started, and antiferroelectric liquid crystal compounds known to date are few.

It is thus a first object of this invention to provide a novel liquid crystal compound having an antiferroelectric phase.

A second object of this invention is to provide a liquid crystal compound that can be used as a liquid crystal display device having tristable switching, sharp threshold and good memory effect.

A third object of this invention is to provide a high-performance liquid crystal compound having high-speed response which compound can be used in a large-sized liquid crystal dislay device.

A fourth object of this invention is to provide a liquid crystal display device using the liquid crystal compound having the aforesaid characteristics.

The other objects of this invention will be clarified from the foregoing description.

MEANS FOR SOLVING THE PROBLEMS

According to the present inventors' studies, it is found that the aforesaid objects and advantages of this invention are achieved by a liquid crystal compound which is a compound (I-a), (I-b) or (I-c) represented by (1) formula (I-a)

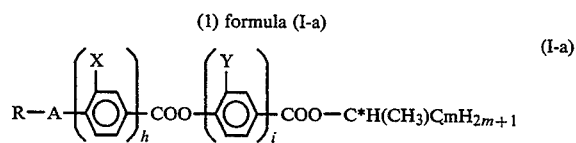

wherein R denotes a linear aliphatic alkyl group having 6 to 14 carbon atoms; A denotes a single bond or an oxygen atom; X and Y independently denote a hydrogen atom or a fluorine atom but they are not hydrogen atoms at the same time; h and i are independently 1 or 2; m is an integer of 3 to 10; and C* denotes an asymmetric carbon atom, (2) formula (I-b)

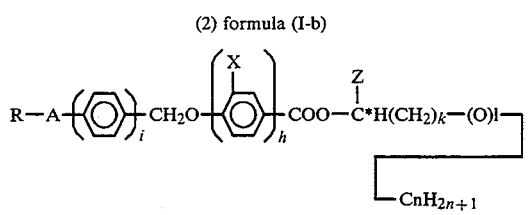

wherein R, A, X, h and i are as defined above; Z denotes $CH_3$, $C_2H_5$ or $CF_3$; k is 0 or an integer of 5 to 8; l is 0 or 1; n is an integer of 1 to 6; and C* denotes an asymmetric carbon atom, or (3) formula (I-c)

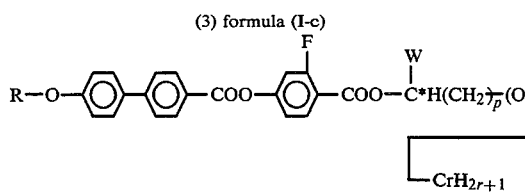

wherein R is as defined above; W denotes $CH_3$ or $CF_3$; when W is $CH_3$, p and q are both 0 and r is 8; when W is $CF_3$, p is 5 to 8, q is 1 and r is 1 to 4; and C* denotes an asymmetric carbon atom.

The liquid crystal compound of this invention is a phenyl ester-type compound represented by formula (I-a), (I-b) or (I-c). The three types of the compounds are described in detail below.

A) Compound (I-a):

The liquid crystal compound (I-a) of this invention is represented by formula (I-a).

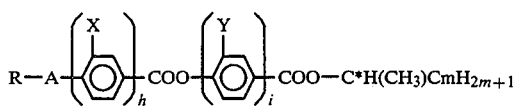

In formula (I-a), R is a linear aliphatic alkyl group having 6 to 14 carbon atoms, preferably 8 to 12 carbon atoms. X and Y are independently a hydrogen atom or a fluorine atom, but they are not hydrogen atoms at the same time. That is, when X is a hydrogen atom, Y is a fluorine atom, or when X is a fluorine atom, Y is a hydrogen atom or a fluorine atom. A is a single bond (—) or an oxygen atom (—O—); the oxygen atom is more preferable. h and i are independently 1 or 2; it is preferable that h is 2 and i is 1. m is an integer of 3 to 10, preferably an integer of 6 to 10. C* is an asymmetric carbon atom.

The compound (I-a) can be formed by the following reaction scheme, for example. However, the compound of this invention is not limited to a compound obtained by this reaction scheme.

(1) Production of a compound wherein A is an oxygen atom:

(i) 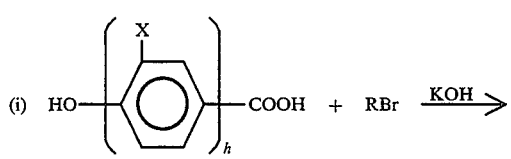

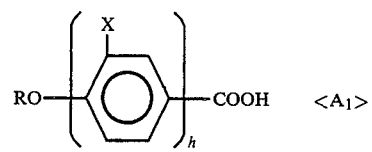

(ii) $CH_3COO$—[ring Y]—$COOH$ $\xrightarrow{SOCl_2}$ $CH_3COO$—[ring Y]—$COCl$ $\xrightarrow{CH_3CH^*(OH)CmH_{2m+1}}$ $CH_3COO$—[ring Y]—$COO$—$C^*H(CH_3)CmH_{2m+1}$ $\xrightarrow{C_6H_5-CH_2NH_2}$ $HO$—[ring Y]—$COO$—$C^*H(CH_3)CmH_{2m+1}$ <A2>

(iii) $RO$—[ring X]—$COOH$ <A1> $\xrightarrow{SOCl_2}$ $RO$—[ring X]—$COCl$ $\xrightarrow{+<A_2>}$ final compound (I-a)

(2) Production of a compound wherein A is a single bond and X is a hydrogen atom

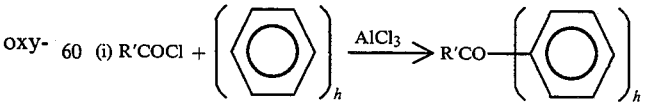

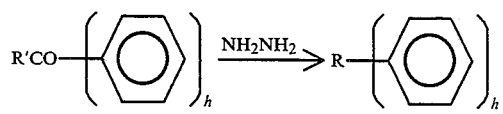

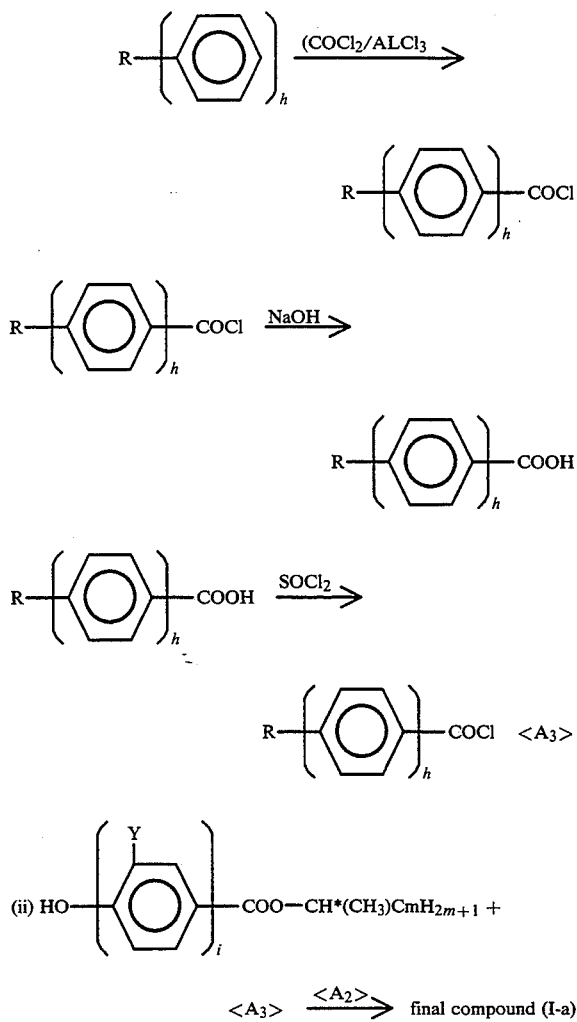

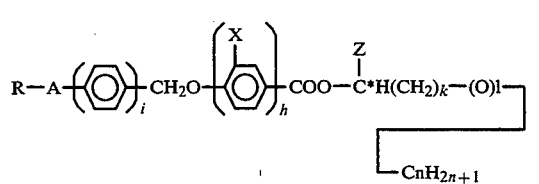

In the reaction schemes shown in (1) and (2), R, A, X, Y, h, i and m are as defined in formula (I-a), and R' is a linear aliphatic alkyl group having 5 to 14 carbon atoms (while R is a linear aliphatic alkyl group having 6 to 14 carbon atoms).

B) Compound (I-b)

The liquid crystal compound (I-a) of this invention is represented by formula (I-b).

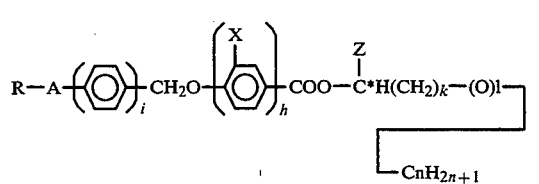

In formula (I-b), R is a linear aliphatic alkyl group having 6 to 14 carbon atoms, preferably 8 to 12 carbon atoms. X is a hydrogen atom or a fluorine atom. Z is $CH_3$, $C_2H_5$ or $CF_3$. A is a single bond (—) or an oxygen atom (—O—); the oxygen atom is preferable. h and i are independently 1 or 2; it is preferable that i is 2 and h is 1. k is 0 or an integer of 5 to 8. l is 0 or 1. n is an integer of 1 to 6. C* is an asymmetric carbon atom.

The compound (I-b) can be formed by the following reaction scheme, for example. However, the compound of this invention is not limited to a compound obtained by this reaction scheme.

Production of a compound (I-b):

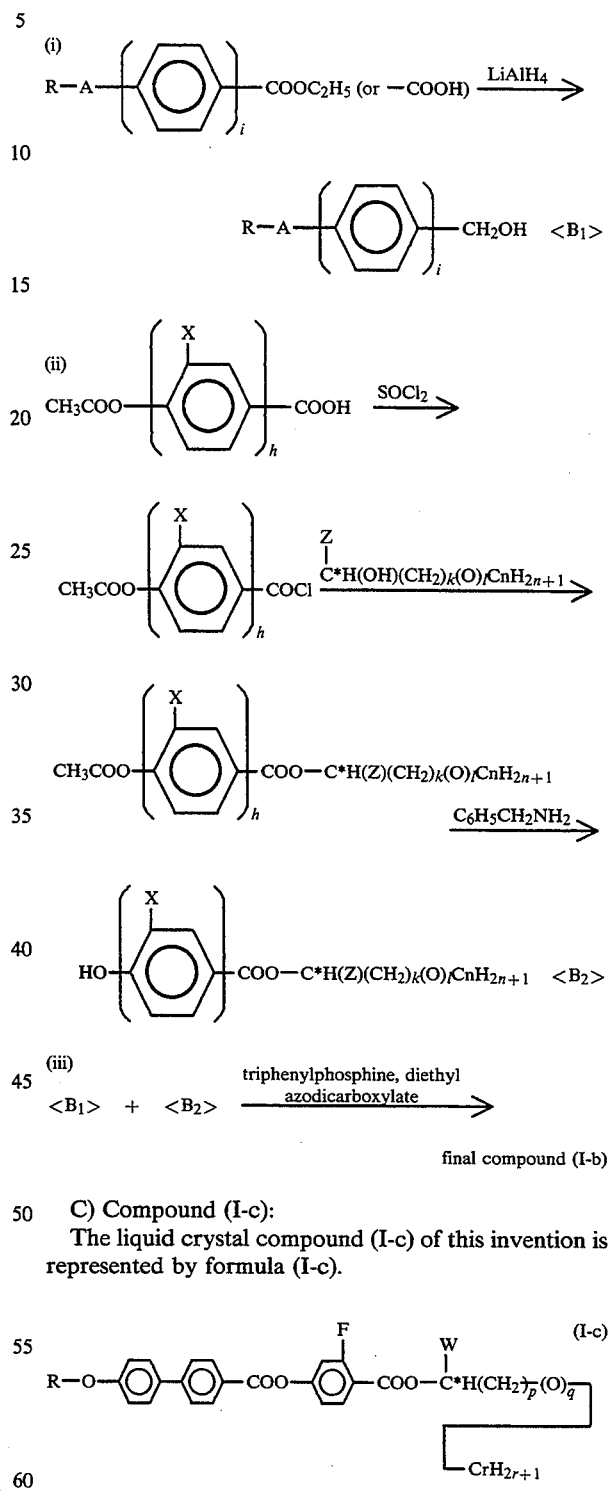

C) Compound (I-c):

The liquid crystal compound (I-c) of this invention is represented by formula (I-c).

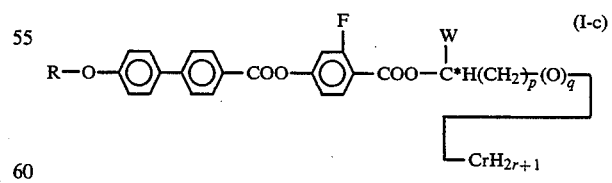

In formula (I-c), R is a linear aliphatic alkyl group having 6 to 14 carbon atoms, preferably 8 to 12 carbon atoms. W is $CH_3$ or $CF_3$. When W is $CH_3$, p and q are both 0 and r is 8; when W is $CF_3$, p is 5 to 8, q is 1 and r is 1 to 4. C* is an asymmetric carbon atom.

The compound (I-c) can be formed by the following reaction scheme. However, the compound of this invention is not limited to a compound obtained by this reaction scheme.

(i) 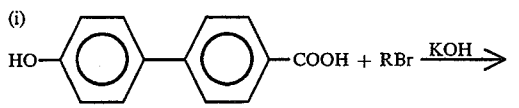

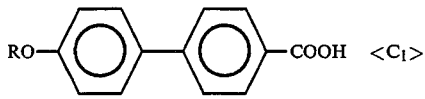

(ii) 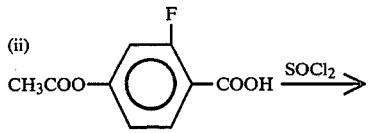

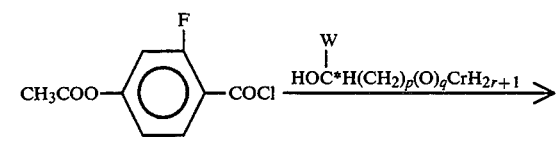

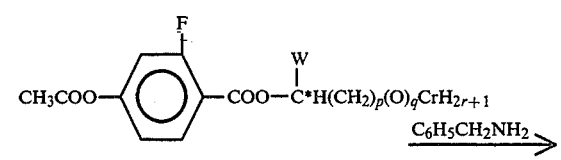

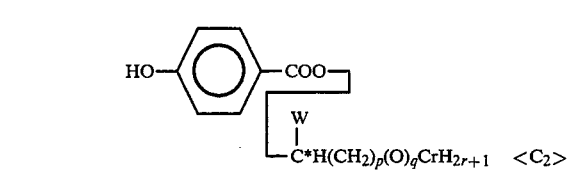

(iii) 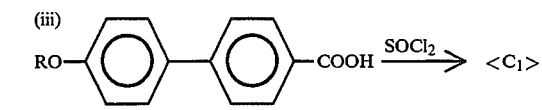

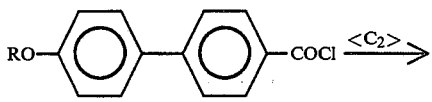

final compound (I-c)

4-Acetoxy-2-fluorobenzoic acid used in the above reaction scheme can be formed by, for example, a method schematically shown below, using m-fluorophenol as a starting material.

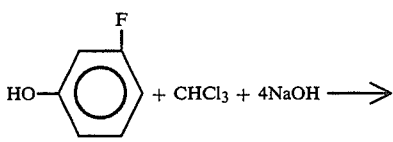

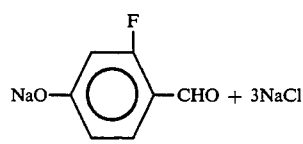

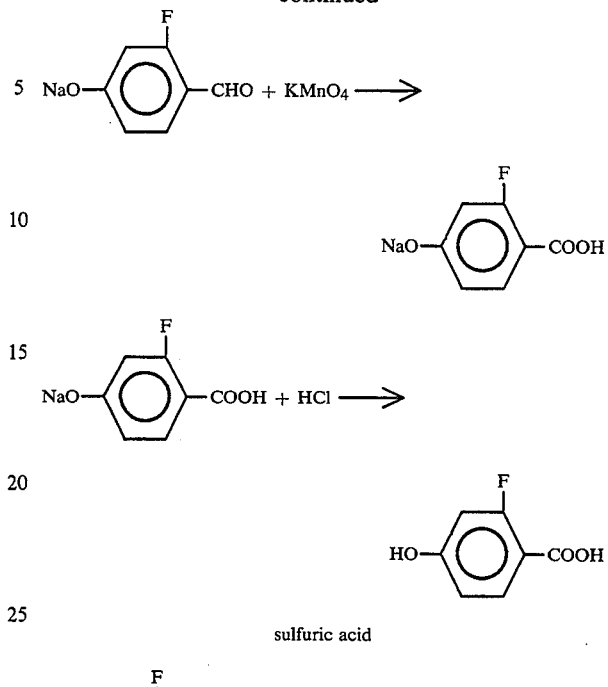

sulfuric acid

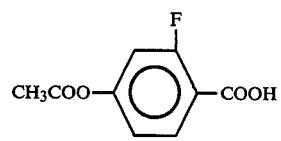

EFFECTS OF THE INVENTION

The phenyl ester-type liquid crystal compounds of formulas (I-a), (I-b) and (I-c) in this invention have all antiferroelectricity. The novel liquid crystal compound provided by this invention can be used in a liquid crystal display device utilizing the characteristics voltage, i.e., high-speed response or tristable switching, sharp threshold and good memory effect.

EXAMPLES

Figure 1:
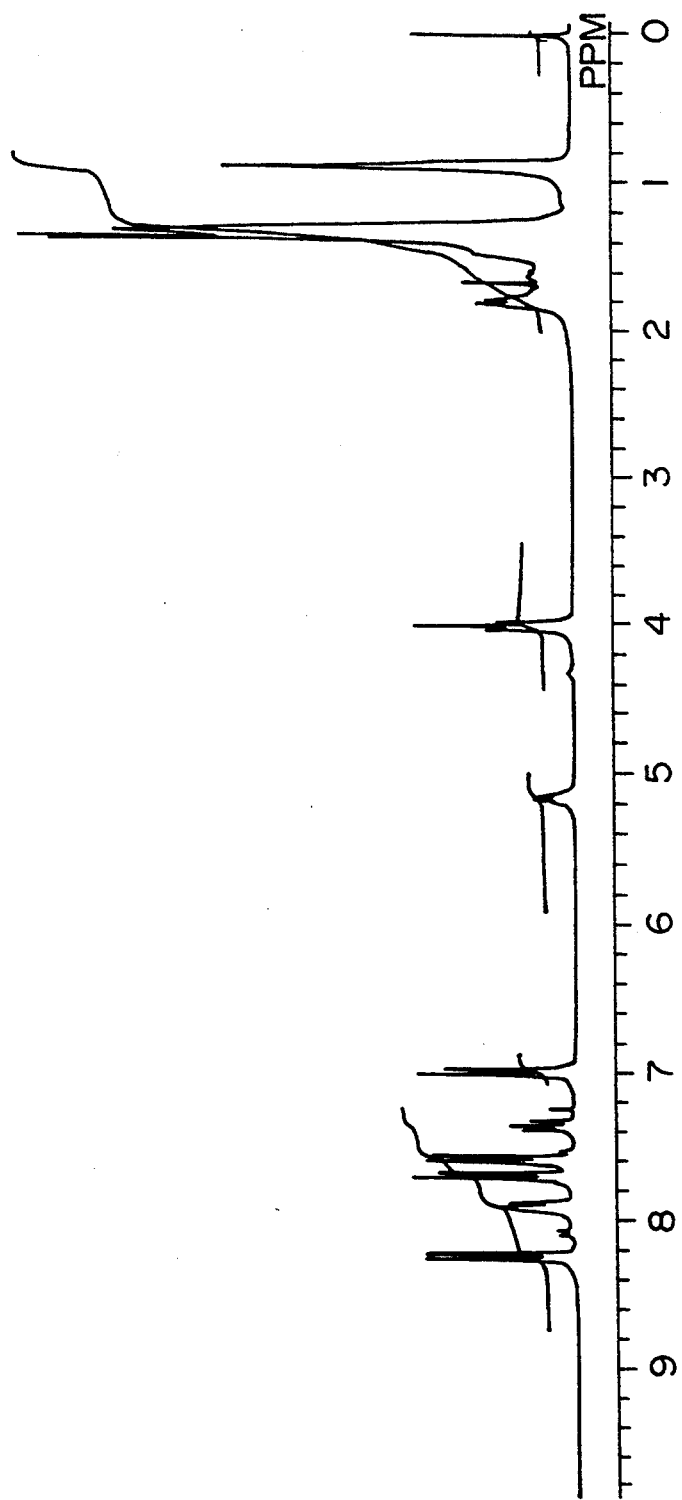
FIG. 1 is an NMR spectrum of a liquid crystal compound obtained in Example 1.

The following Examples and Comparative Examples illustrate this invention more specifically. This invention is, of course, not limited thereto.

EXAMPLE 1

Production of 2-fluoro-4-(1-methylheptyloxycarbonyl)phenyl 4'-octyloxybiphenyl-4-carboxylate

[In formula (1-a), R=$C_8H_{17}$, A=0, h=2, i=1, X=H, Y=F, m=6]

1) Production of 4-(4'-n-octyloxy)biphenylcarboxylic acid (1)

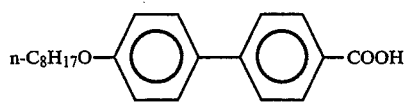

4-(4'-Hydroxy)biphenylcarboxylic acid (10.5 g), 14.0 g of n-octyl bromide, and 6.45 g of potassium hydroxide were added to a mixed solution of 1,500 ml of ethanol and 200 ml of water, and they were reacted under reflux for 10 hours. Further, 500 ml of water was added, and the mixture was stirred for 3 hours. After the reaction was over, the reaction mixture was acidified with conc. hydrochloric acid. Then, 500 ml of the solvent was evaporated, and the residue was cooled to room temperature to obtain a white solid. The white solid was washed well with water, and then recrystallized with chloroform to provide 12.0 g of a final product (1) as a white crystal.

2) Production of 4-acetoxy-3-fluorobenzoic acid (2)

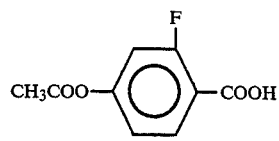

3-Fluoro-4-hydroxybenzoic acid (4.3 g) and 8.4 g of anhydrous acetic acid were charged into a two-necked flask and mixed. Five drops of sulfuric acid were added under ice cooling. After heat generation stopped, the mixture was heated at 80° C. for 30 minutes. Subsequently, the reaction mixture was charged in cold water, and precipitated crystals were filtered. The crystals were vacuum-dried and then used in the next step. The yielded amount was 4.8 g.

3) Production of 4-acetoxy-3-fluoro-1-(1-methylheptyloxycarbonyl)benzene (3)

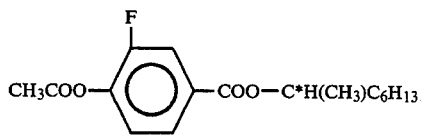

4-Acetoxy-3-fluorobenzoic acid (1.2 g) was added to 7 ml of thionyl chloride, and they were reacted under reflux for 5 hours. After excess thionyl chloride was evaporated, a mixture of 1 ml of pyridine, 4 ml of dry ether and 0.5 g of S-(+)-2-octanol was added dropwise. After the dropwise addition, the mixture was stirred at room temperature for 24 hours, and diluted with 200 ml of ether. The organic layer was washed with dilute hydrochloric acid, a 1N sodium hydroxide aqueous solution and water in this sequence, and dried over magnesium sulfate. The solvent was evaporated, and a crude product was purified by silica gel column chromatography using a hexane/ethyl acetate solvent mixture to obtain 1.1 g of a final product (3).

4) Production of 4-hydroxy-3-fluoro-(1-methylheptyloxycarbonyl)benzene (4)

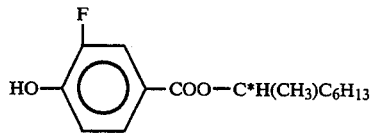

The above compound (3) (1.1 g) was dissolved in 30 ml of ethanol, and 3 g of benzylamine was added dropwise. The mixture was stirred at room temperature for 24 hours, then diluted with 300 ml of ether, washed with dilute hydrochloric acid and water in this sequence, and dried over magnesium sulfate. After the solvent was evaporated, the solid was purified by silica gel column chromatograhy to afford 0.6 g of a final product (4).

5) Production of 2-fluoro-4-(1-methylheptyloxycarbonyl)phenyl 4'-n-octyloxybiphenyl-4-carboxylate (5)

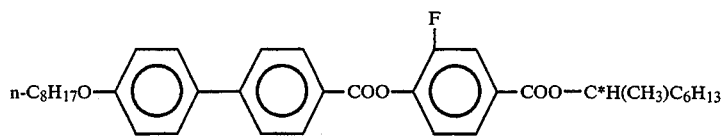

Ten milliliters of thionyl chloride were added to 0.9 g of the above compound (1), and heat-refluxed for 10 hours. After excess thionyl chloride was evaporated, 10 ml of pyridine and 25 ml of toluene were added, and 25 ml of a benzene solution containing 0.5 g of the above compound (4) was then added dropwise, followed by conducting the reaction at room temperature. After the reaction was over, the reaction mixture was diluted with 300 ml of ether, and washed with dilute hydrochloric acid, a 1N sodium carbonate aqueous solution and water in this sequence. The organic layer was dried over magnesium sulfate. After the solvent was evaporated, the solid was then purified by silica gel column chromatograhy, and then recrystallized with ethanol to obtain 0.6 g of a final product (5). An NMR spectrum of the final product (5) is shown in FIG. 1. Identification of phases was carried out by observation of a texture and measurement with DSC (differential scanning calorimeter).

Phase transition temperatures of the compound (5) are as follows. An antiferroelectric phase was observed in this compound.

crystal $\xleftarrow{30°\ C.}$ $S_X$ $\xleftarrow{31°\ C.}$ $S_{CA^*}$ $\xleftarrow{51°\ C.}$ $S_A$ $\xleftarrow{118°\ C.}$ isotropic phase wherein $S_X$ is an unidentified smectic phase, $S_{CA}$ is an antiferroelectric phase, and $S_A$ is a smectic phase.

6) A liquid crystal cell (a cell thickness 3 micrometers) with an ITO electrode having a rubbed polyimide thin film was filled with the compound (5) in an isotropic phase. The cell was slowly cooled at a rate of 1.0° C. per minute, and the liquid crystal was aligned in an $S_A$ phase. The cell was disposed between intersecting deflection plates such that the layer direction of the liquid crystal was parallel to an analyzer or a polarizer. A triangular wave voltage of ±40 V and 0.2 Hz was applied to the cell and change in transmittance was measured by a photomultiplier. As a result, a double hysteresis peculiar to the antiferroelectric phase was observed in a temperature region of from 50° C. to 30° C.

Figure 2:
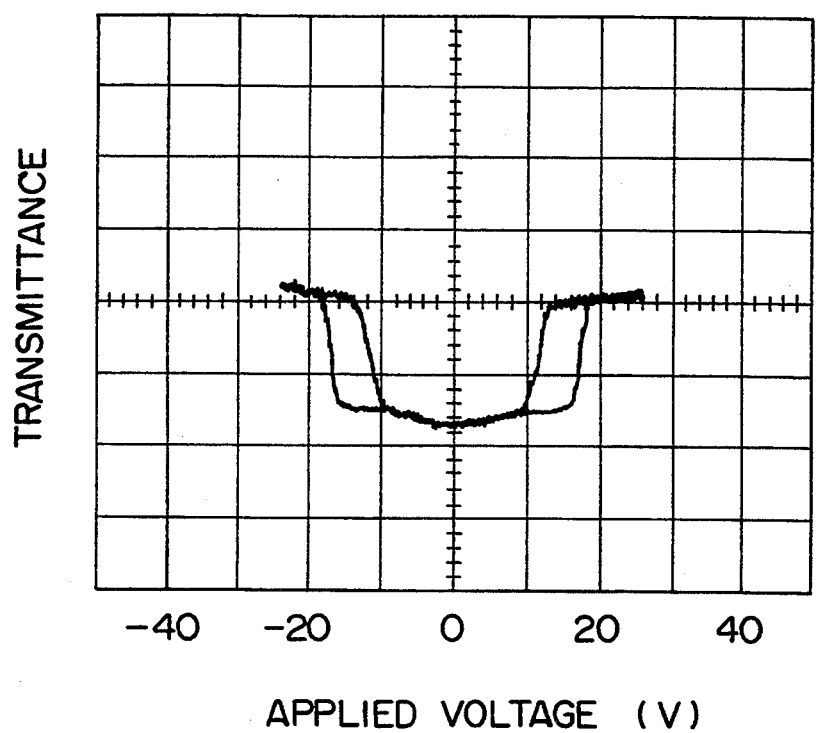
FIG. 2 is a graph showing optical response hysteresis of the liquid crystal compound obtained in Example 1.

An optical response hysteresis at 50° C. is shown in FIG. 2.

EXAMPLES 2 and 3

In the same way as in Example 1, liquid crystal compounds represented by the following formulas were produced except using S-(+)-2-hexanol and S-(+)-2-decanol respectively instead of S-(+)-2-octanol.

(Example 2)

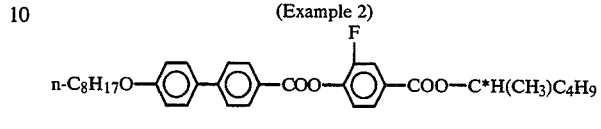

(Example 3)

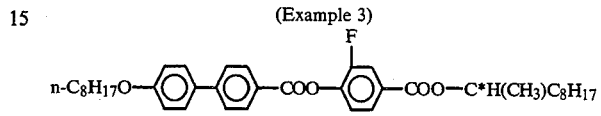

Figure 3:
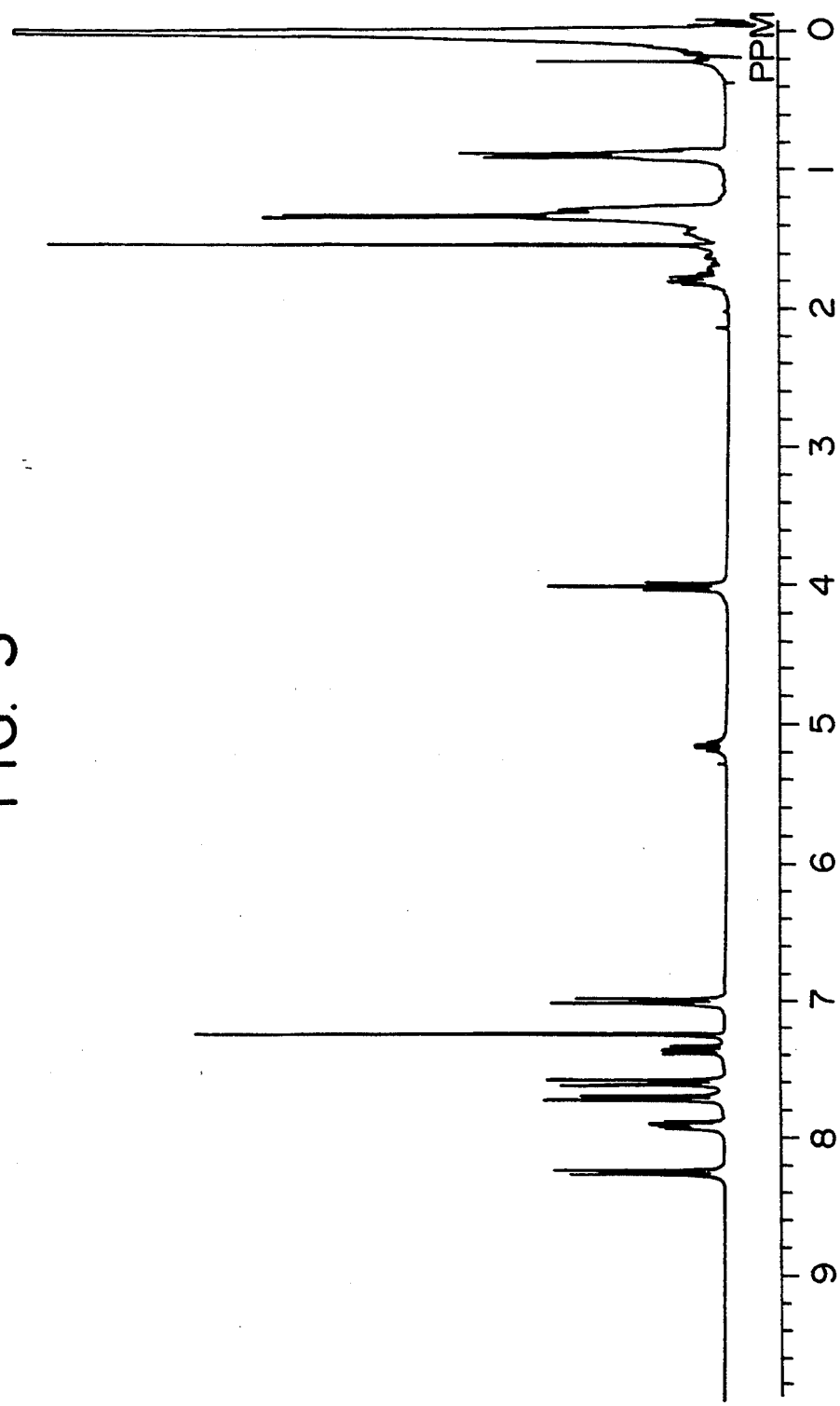
FIG. 3 is an NMR spectrum of the liquid crystal compound obtained in Example 2.
Figure 4:
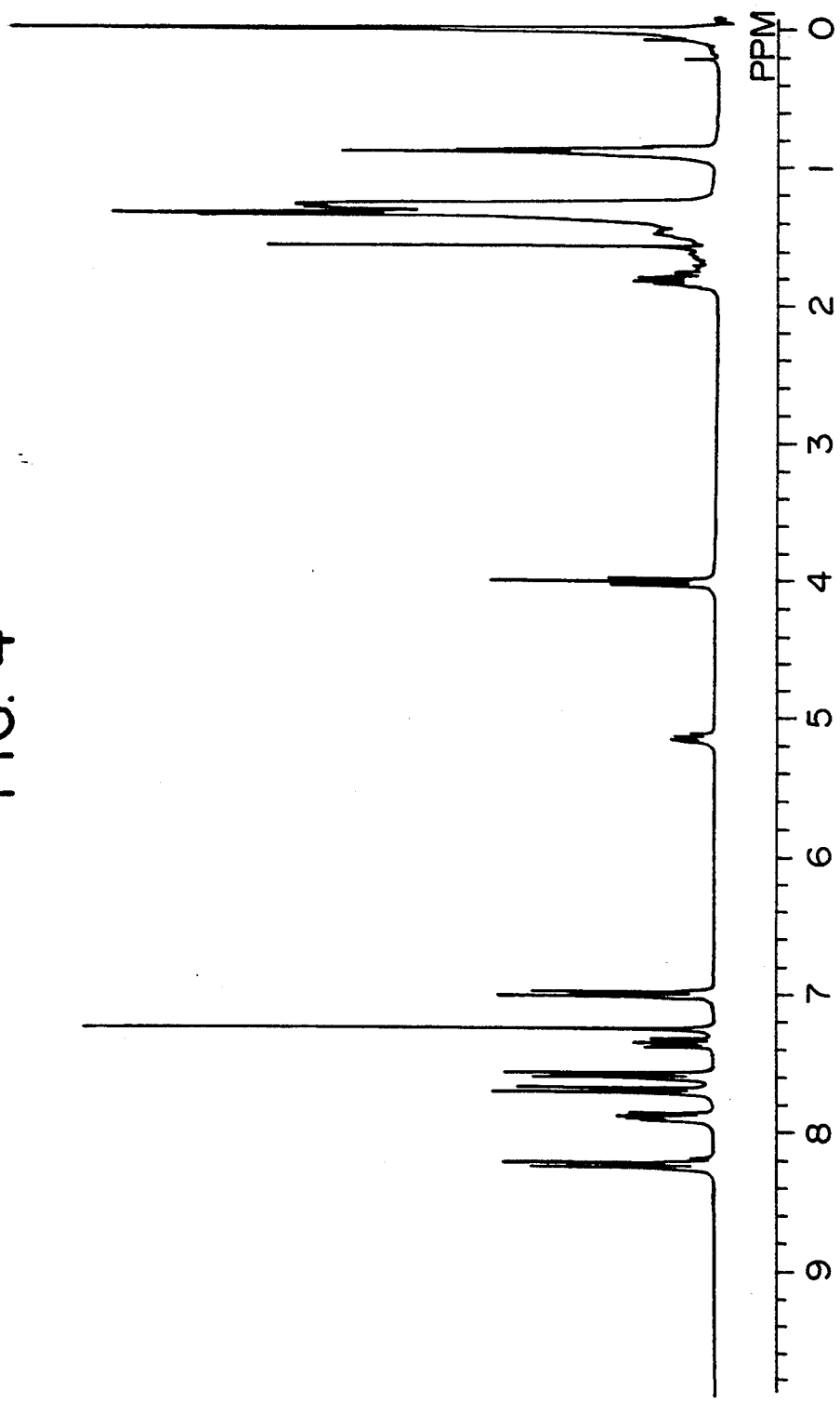
FIG. 4 is an NMR spectrum of the liquid crystal compound obtained in Example 3.

NMR spectra of these liquid crystal compounds are shown in FIGS. 3 and 4.

Identification of phases was conducted by observation of a texture and measurement with DSC.

Phase transition temperatures of these two compounds are shown in Table 1. They were found to have an antiferroelectric phase.

TABLE 1

| Example No. | Phase transition temperatures |
|---|---|
| 2 | crystal $\xleftarrow{29°\ C.}$ $S_Y$ $\xleftarrow{32°\ C.}$ $S_X$ $\xleftarrow{34°\ C.}$ $S_{CA^*}$ $\xleftarrow{70°\ C.}$ $S_A$ $\xleftarrow{130°\ C.}$ isotropic phase |
| 3 | crystal $\xleftarrow{37°\ C.}$ $S_{CA^*}$ $\xleftarrow{77°\ C.}$ $S_A$ $\xleftarrow{104°\ C.}$ isotropic phase |

In Table 1, $S_X$ and $S_Y$ are unidentified phases.

In the same way as in 6) of Example 1, optical response of said compounds was observed. As a result, they were found to have a double hysteresis peculiar to the antiferroelectric phase.

Furthermore, the response speed of the compound of Example 2 was measured under the following conditions: at a temperature lower than the smectic A phase-→antiferroelectric phase transition temperature by 10° C.; cell length of 2 μm; and under an applied voltage of 10 V over the threshold value. (The response speed from the antiferroelectric phase to the ferroelectric phase is defined to be the time that lapses while the transmittance changes from 10% to 90%; and the response speed from ferroelectric state to the antiferroelectric phase, to be the time that lapses while the transmittance changes from 90% to 10%.) Consequently, the response speed from the antiferroelectric phase to ferroelectric phase and that from the ferroelectric phase to anti-ferroelectric phase were, respectively, 8 and 5 μsec.

Response speeds (response speed from the antiferroelectric state to the ferroelectric state is defined to be a time that lapses when transmittance is changed from 10% to 90%, and response speed from the ferroelectric state to the antiferroelectric state is defined to be a time that lapses when transmittance is changed from 90% to 10%) were measured using a 2-micrometer thick electrode cell. As a result, the response speed from the antiferroelectric state to the ferroelectric sate was 8 μsec, and that from the ferroelectric state to the antiferroelectric state was 5 μsec.

EXAMPLES 4 and 5

In the same way as in Example 1, liquid crystal compounds represented by the following formulas were produced except using 4-(4'-n-undecyloxy)biphenylcarboxylic acid and 4-(4'-n-tetradecyloxy)biphenylcarboxylic acid respectively instead of 4-(4'-n-octyloxy)biphenylcarboxylic acid.

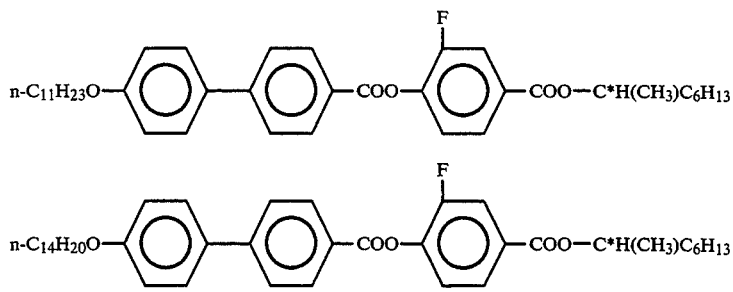

(Example 4)

(Example 5)

Figure 5:
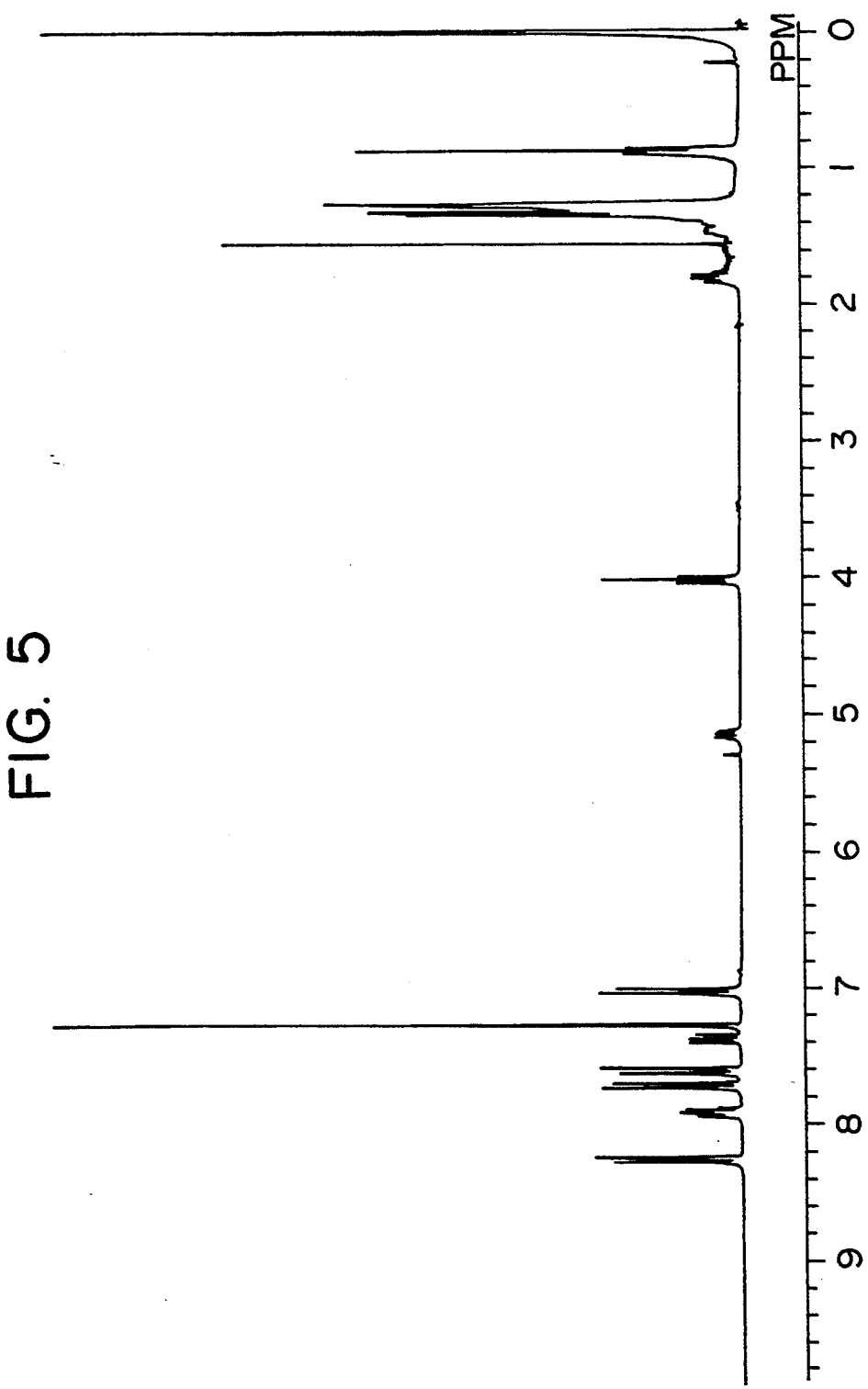
FIG. 5 is an NMR spectrum of the liquid crystal compound obtained in Example 4.
Figure 6:
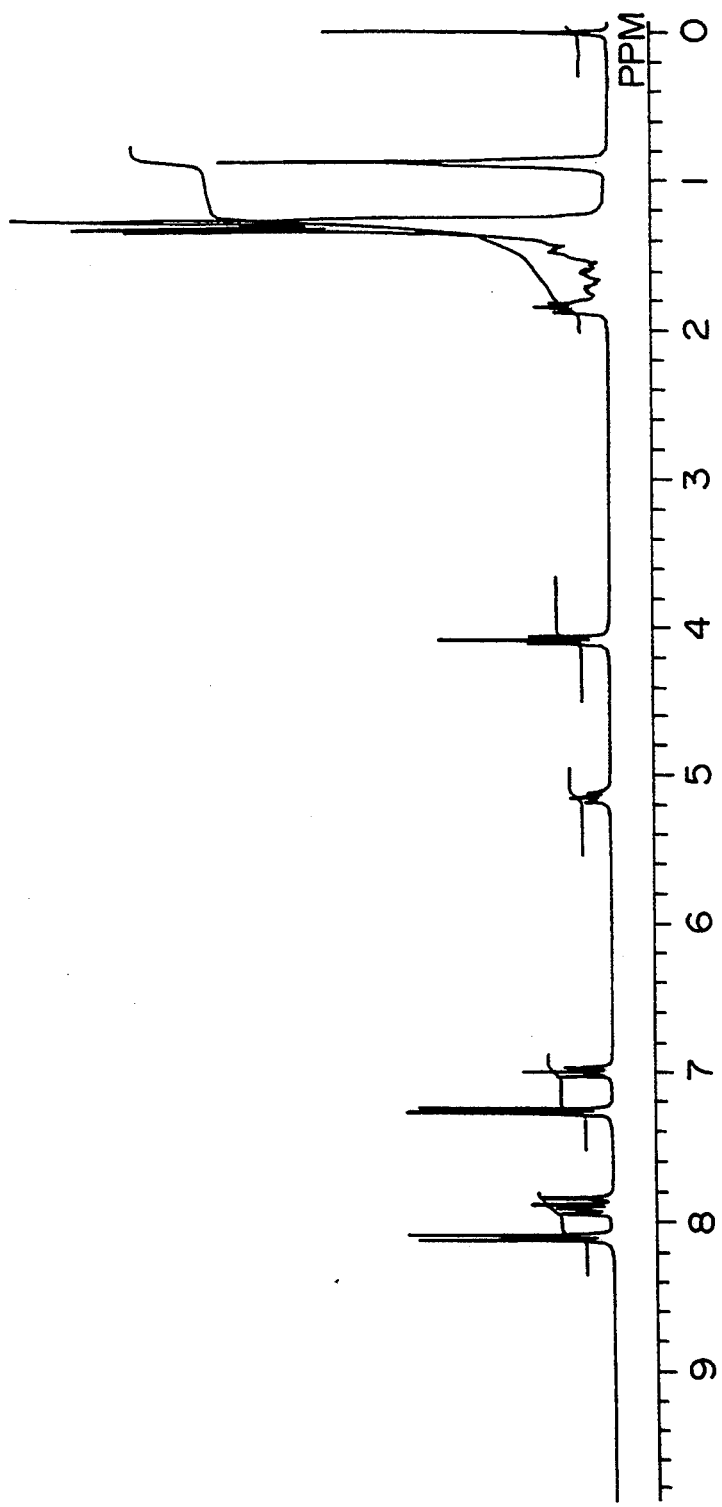
FIG. 6 is an NMR spectrum of the liquid crystal compound obtained in Example 5.

NMR spectra of these liquid crystal compounds are shown in FIGS. 5 and 6. Identification of phases was carried out by observation of a texture and measurement with DSC.

Phase transition temperatures of the compounds are shown in Table 2. They were found to have an antiferroelectric phase.

TABLE 2

| Example No. | Phase transition temperatures |
| --- | --- |
| 4 | crystal ⇄ 21° C. $S_{CA*}$ ⇄ 66° C. $S_{C*}$ ⇄ 86° C. $S_A$ ⇄ 103° C. isotropic phase |
| 5 | crystal ⇄ 33° C. $S_{CA*}$ ⇄ 87° C. $S_A$ ⇄ 95° C. isotropic phase |

In the same way as in (6) of Example 1, optical response of the compounds was measured. As a result, they were found to have a double hysteresis peculiar to the antiferroelectric phase.

EXAMPLE 6

Production of 4-(1-methylheptyloxycarbonyl)biphenyl 3'-fluoro-4'-decyloxybenzoate

[In formula (I-a), R=C₁₀H₂₁, A=0, h=1, i=2, X=F, Y=H, m=6]

(1) Production of 3-fluoro-4-decyloxybenzoic acid (1)

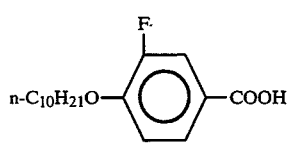

A mixture of 1 g of 3-fluoro-4-hydroxybenzoic acid, 1.5 g of decyl bromide, 0.8 g of potassium hydroxide and 100 ml of ethanol was stirred under reflux for 6 hours. Two-hundred milliliters of water were added, and the mixture was further stirred under reflux for 2 hours. The reaction mixture was cooled, acidified with hydrochloric acid and then extracted with dichloromethane. The organic layer was dried over magnesium sulfate, and the solvent was then evaporated. To the residue was added 100 ml of isooctane, and the mixture was cooled. The precipitated crystals were filtered, and dried to obtain 0.7 g of a final product (1).

(2) Production of 4'-acetoxy-4-(1-methylheptyloxycarbonyl)biphenyl (2)

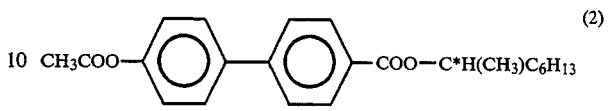

Ten milliliters of thionyl chloride were added to 3.0 g of 4'-acetoxy-4-biphenylcarboxylic acid, and the mixture was refluxed for 6 hours. Excess thionyl chloride was then completely evaporated. The obtained acid chloride was dissolved in 50 ml of toluene, and 5 ml of pyridine was further added. To the solution was added dropwise 1.0 g of S-(+)-2-octanol. The mixture was refluxed for 18 hours, and then allowed to cool. One hundred milliliters of dichloromethane were added, and the mixture was washed with hydrochloric acid, a sodium hydroxide aqueous solution and water in this sequence. After drying, the solvent was removed, and the solid was purified by silica gel column chromatography to obtain 0.2 g of a final product (2).

(3) Production of 4'-hydroxy-4-(1-methylheptyloxycarbonyl)biphenyl (3)

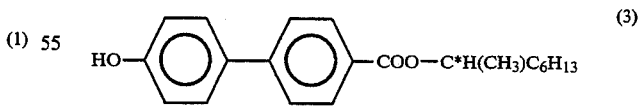

To the above compound (2) were added 15 ml of ethanol and 2.0 g of benzylamine, and they were stirred at room temperature for 24 hours. Fifty milliliters of dichloromethane were added, and the mixture was washed with hydrochloric acid and water. After drying, the solvent was removed, and the solid was purified by silica gel column chromatography to afford 1.6 g of a final product (3).

(4) Production of 4-(1-methylheptyloxycarbonyl)-biphenyl 3'-fluoro-4'-decyloxybenzoate (4)

$$\text{n-C}_{10}\text{H}_{21}\text{O}-\underset{F}{\underset{|}{\bigcirc}}-\text{COO}-\bigcirc-\bigcirc-\text{COO}-\text{C*H(CH}_3\text{)C}_6\text{H}_{13} \quad (4)$$

3-Fluoro-4-decyloxybenzoic acid (0.7 g) was chlorinated with 10 ml of thionyl chloride as in (1). To the obtained acid chloride were added 20 ml of toluene and 4 ml of pyridine, followed by adding 0.5 g of the compound (2). The mixture was stirred at room temperature for 24 hours, and 50 ml of dichloromethane was added. The reaction mixture was washed with hydrochloric acid, a sodium hydroxide aqueous solution and water in this sequence, and then dried. The solvent was removed, and the solid was purified by silica gel column chromatography to obtain 3 g of a final product (4).

Figure 7:
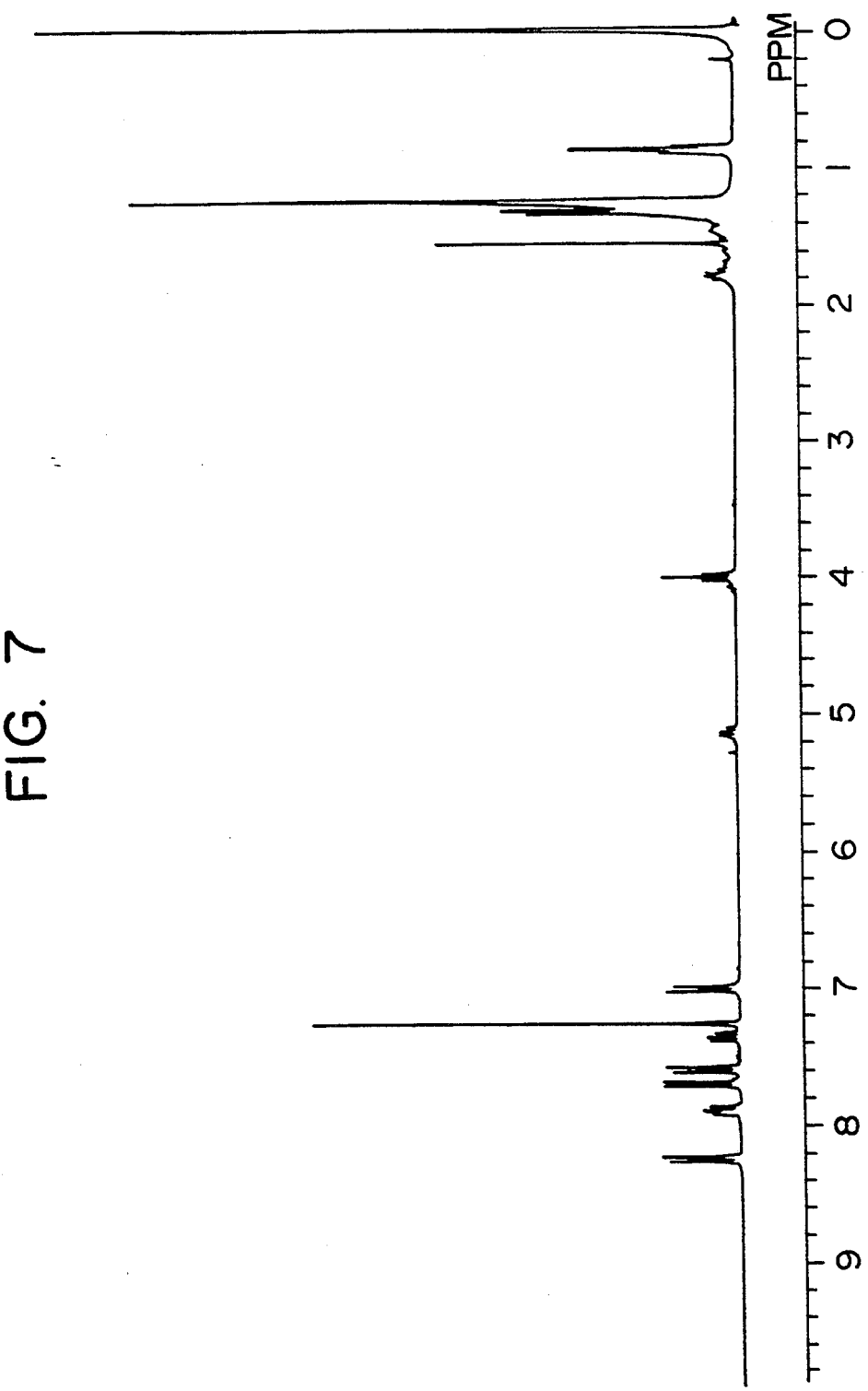
FIG. 7 is an NMR spectrum of the liquid crystal compound obtained in Example 6.

An NMR spectrum of the final product (4) is shown in FIG. 7.

Identification of phases was carried out by observation of a texture and measurement with DSC.

Phase transition temperatures of the compound (4) are as follows. The compound (4) was found to have a chiral smectic phase being a ferroelectric phase and an antiferroelectric phase.

$$\text{crystal} \xleftarrow{42° C.} S_{CA*} \xleftarrow{68° C.} S_{C*} \xleftarrow{100° C.} S_A \xleftarrow{116° C.} \text{isotropic phase}$$

(5) Optical response of the compound (4) was measured as in 6) of Example 1. As a result, the compound was found to have a double hysteresis peculiar to an antiferroelectric phase.

EXAMPLE 7

Production of 4-(1-methylheptyloxycarbonyl)phenyl 3'-fluoro-4'-decyloxybenzoate

[In formula (I-a), R=$C_{10}H_{21}$, A=0, h=1, i=1, X=F, Y=H, m=6]

4-Hydroxy-(1-methylheptyloxycarbonyl)benzene was produced as in Example 1. Said benzene and the compound (1) obtained in Example 3 were coupled as in Example 1 to obtain a final product.

Figure 8:
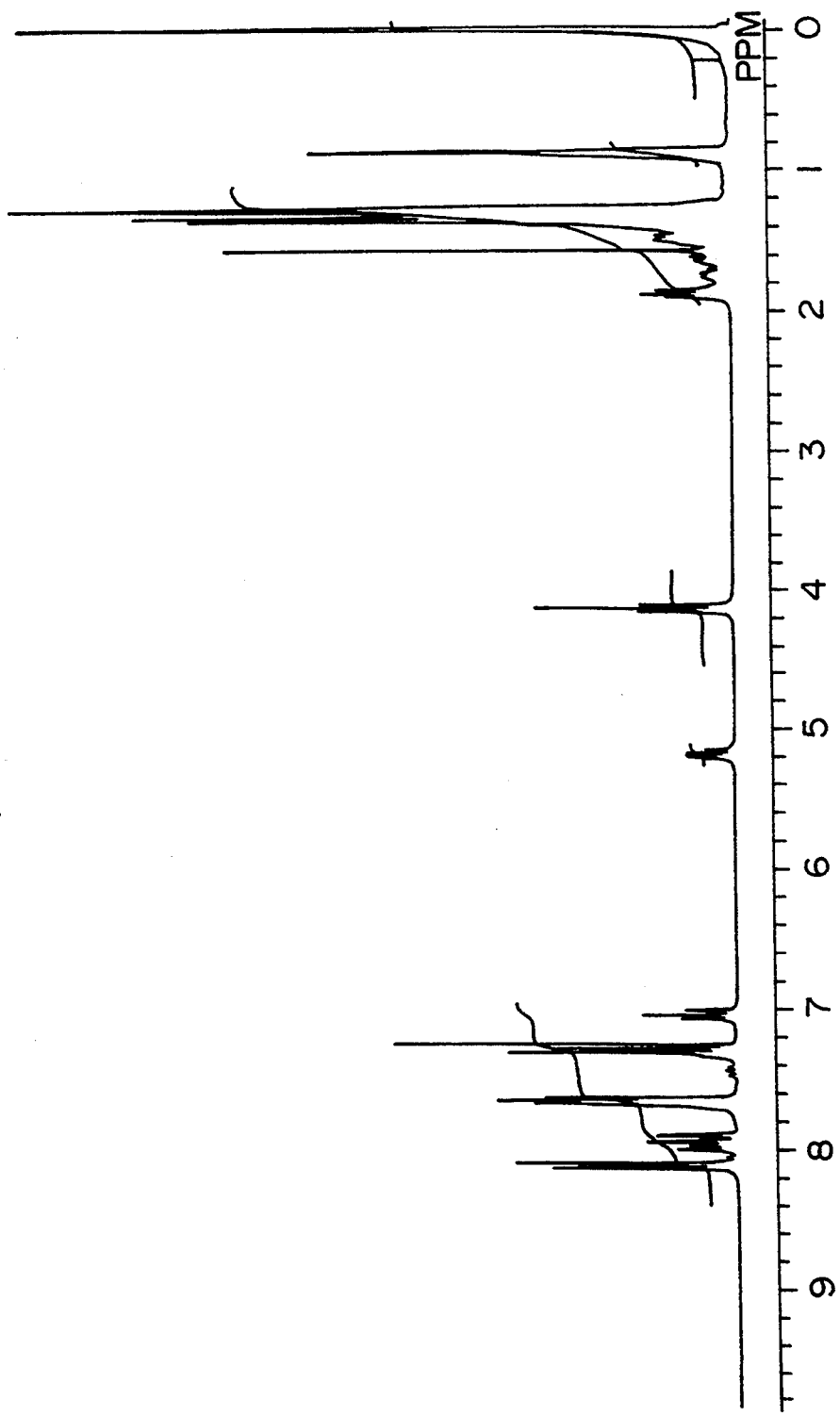
FIG. 8 is an NMR spectrum of the liquid crystal compound obtained in Example 7.

An NMR spectrum of the final product is shown in FIG. 8. Identification of phases was carried out by observation of a texture and measurement with DSC.

Phase transition temperatures of the compound are as follows. Said compound was found to have a chiral smectic phase being a ferroelectric phase. The chiral smectic phase is in a quite low temperature region, and the compound is available as an effective ingredient to enlarge a temperature of a liquid crystal phase to a low temperature side.

$$\text{crystal} \xleftarrow{-18° C.} S_{C*} \xleftarrow{1° C.} \text{isotropic phase}$$

wherein $S_C*$ is a chiral smectic phase.

COMPARATIVE EXAMPLE 1

Production of 4-(1-methylpentyloxycarbonyl)phenyl 4'-octyloxybiphenyl-4-carboxylate

[In formula (I-a), R=$C_8H_{17}$, A=0, h=2, i=1, X=H, Y=H, m=4]

In the same way as in Example 1, 4-(1-methylpentyloxycarbonylphenyl) 4'-octyloxybiphenyl-4-carboxylate was produced as in Example 1 except using 2-hexanol and p-hydroxybenzoic acid instead of 2-octanol and 3-fluoro-4--hydroxybenzoic acid.

Phase transition tempepratures of this compound is as follows, and it was found to have an antiferroelectric phase.

$$\text{crystal} \xleftarrow{55° C.} S_{IA*} \xleftarrow{67° C.} S_{CA*} \xleftarrow{125° C.} S_A \xleftarrow{158° C.} \text{isotropic phase}$$

Response speed of this compound was measured as in Example 2. Consequently, response speed from the antiferro electric phase to the ferroelectric phase was 15 microseconds, and response speed from the ferroelectric phase to the antiferroelectric phase was 30 microseconds. This reveals that the fluorinated compound in Example 2 is quite high in response speed.

EXAMPLE 8

Production of 6-ethoxy-1-trifluoromethylhexyl 4'-(4-octyloxyphenylmethoxy)biphenyl-4-carboxylate

[In formula (I-b), R=$C_8H_{17}$, A=0, i=1, h=2, X=H, Z=$CF_3$, k=5, l=1, n=2]

1) Production of p-octyloxybenzyl alcohol (1)

$$\text{n-C}_8\text{H}_{17}\text{O}-\bigcirc-\text{CH}_2\text{OH} \quad (1)$$

Ethyl p-octyloxybenzoate (25 mmols) was dissolved in 200 ml of tetrahydrofuran, and 38 mmols of lithium aluminium hydride were added. The solution was stirred at room temperature for 2 hours. Subsequently, in order to decompose unreacted lithium aluminium hydride, water was added dropwise. The mixture was acidified with a hydrochloric acid aqueous solution and extracted with ether. The organic layer was dried and concentrated. The solid was purified by silica gel column chromatography using a solvent mixture of ethyl acetate and hexane (this solvent mixture was used in the following Examples) to afford a final product (1) in a yield of 69%, 2) Production of 6-ethoxy-1-trifluoromethylhexyl 4'-hydroxybiphenyl-4-carboxylate (2)

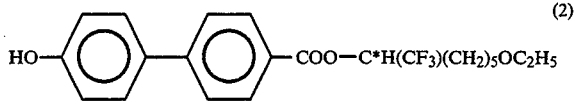
(2)

Thionyl chloride (0.14 mol) was added to 9.8 mmols of 4'-acetoxybiphenyl-4-carboxylic acid, and the mixture was refluxed for 6 hours. Excess thionyl chloride was then completely evaporated. The obtained acid chloride was dissolved in 50 ml of toluene. Five milliliters of pyridine and 9 mmols of R-(+)-7-ethoxy-1,1,1-trifluoro-2-heptanol were added dropwise, and the solution was heat-refluxed for 18 hours. Said solution was left to cool, and 100 ml of dichloromethane was added. The organic layer was washed with a hydrochloric acid aqueous solution, a sodium hydroxide aqueous solution and water in this sequence. After drying, the solvent was removed, and the solid was purified by silica gel column chromatography to obtain 6-ethoxy-1-trifluoromethylhexyl 4'-acetoxybiphenyl-4-carboxylate in a yield of 85%.

Ethanol (15 ml) was added to 5.55 mmols of said carboxylate, and 12 mmols of benzylamine were added dropwise, followed by stirring the mixture overnight at room temperature. One hundred milliliters of dichloroethane were added to the reaction solution, and the mixture was washed with a hydrochloric acid aqueous solution and water. After drying, the solvent was removed, and the solid was purified by silica gel column chromatography to obtain 6-ethoxy-1-trifluoromethylhexyl 4'-hydroxybiphenyl-4-carboxylate in a yield of 91%.

3) Production of 6-ethoxy-1-trifluoromethylhexyl 4'-(4-octyloxyphenylmethoxy)biphenyl-4-carboxylate (3)

Triphenylphosphine (2.8 mmols) was added to a tetrahydrofuran solution of 2.8 mmols of the compound (1) and 26 ml of the compound (2), and 4 mmols of ethyl azodicarboxylate were then added dropwise. The mixture was stirred at room temperature for 45 minutes. After tetrahydrofuran was distilled off at room temperature under reduced pressure, part of the product was purified by silica gel column chromatograhy.

Figure 9:
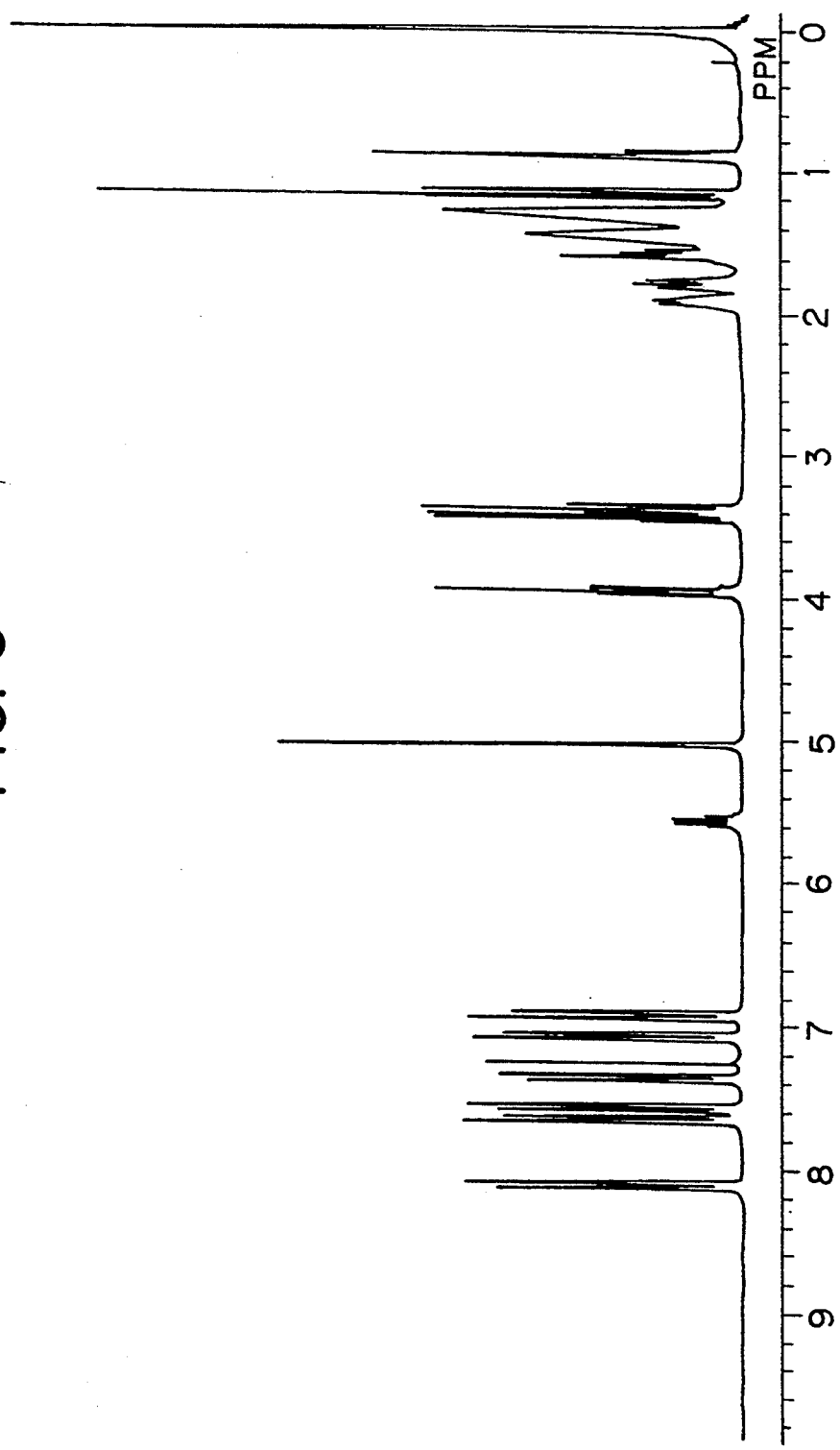
FIG. 9 is an NMR spectrum of the liquid crystal compound obtained in Example 8.

An NMR spectrum of the purified product is shown in FIG. 9.

Identification of phases was carried out by observation of a texture and measurement with DSC.

Phase transition temperatures of the compound (3) are as follows. Said compound was found to have an antiferroelectric phase.

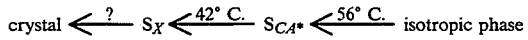

wherein $S_{CA^*}$ is an antiferroelectric phase and $S_X$ is an unidentified smectic phase.

4) Optical response was measured same as in Example 1–6). Response speed were measured same as in Example 2. As a result, a double hysteresis peculiar to the antiferroelectric phase was observed in a temperature region of from 55° C. to 45° C.

Figure 10:
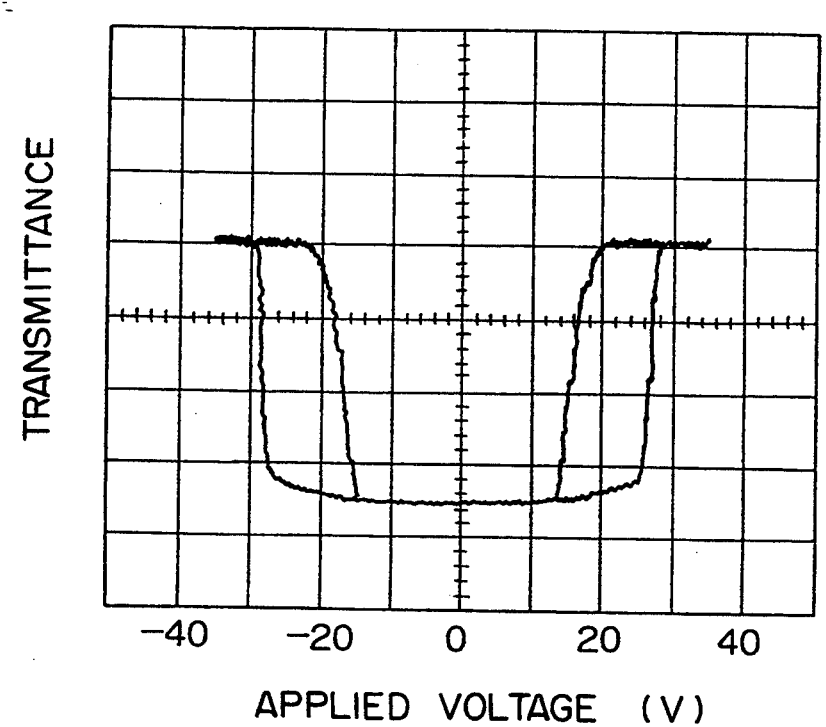
FIG. 10 is an optical response hysteresis of the liquid crystal compound obtained in Example 8.

An optical resonse hysteresis at 45° C. is shown in FIG. 10.

As a result, the response speed from the antiferroelectric state to the ferroelectric state was 370 microseconds, and that from the ferroelectric state to the antiferroelectric state was 540 microseconds; they were both high response speeds.

EXAMPLE 9

A liquid crystal compound represented by the following formula was produced as in Example 8 except using R-(+)-9-ethoxy-1,1,1-trifluoro-2-nonanol instead of R-(+)-7-ethoxy-1,1,1-trifluoro-2-heptanol.

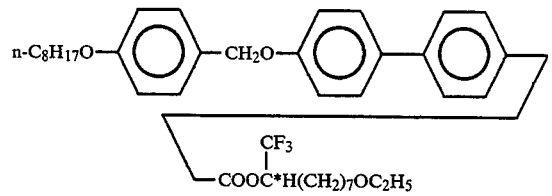

Figure 11:
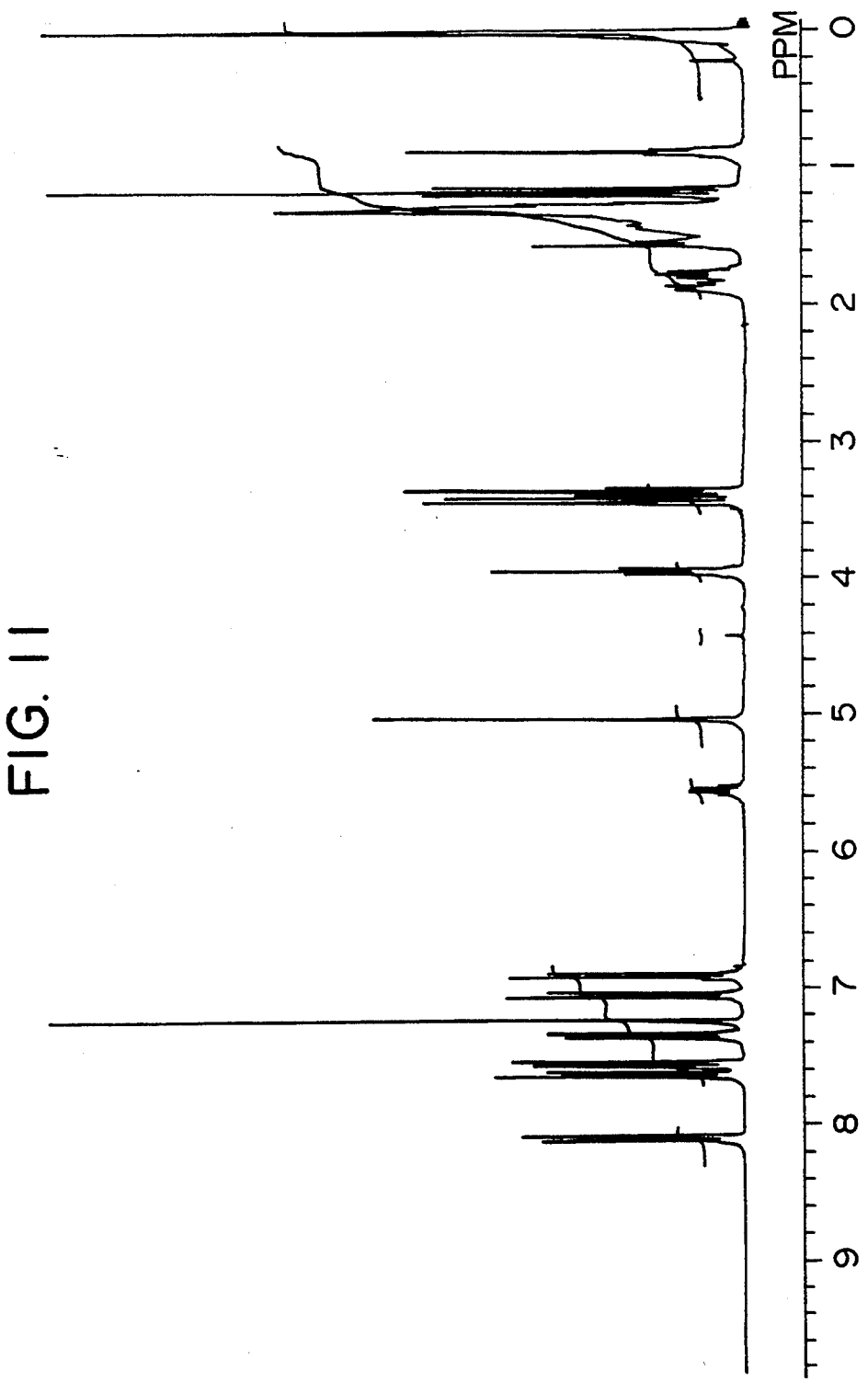
FIG. 11 is an NMR sectrum of the liquid crystal compound obtained in Example 9.

An NMR spectrum of the purified product is shown in FIG. 11.

Identification of phases was conducted by observation of a texture and measurement with DSC.

Phase transition temperatures of the compound is as follows. It was found to have an antiferroelectric phase.

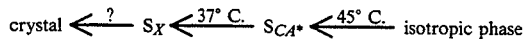

Response speeds were measured at 40° C. as in Example 2. As a result, the response speed from the antiferroelectric state to the ferroelectric state was 310 microseconds, and that from the ferroelectric state to the antiferroelectric state was 620 microseconds.

EXAMPLE 10

Production of 6-ethoxy-1-trifluoromethylhexyl 4'-(4-octylphenylmethoxy)biphenyl-4-carboxylate

[In formula (1-b), R=$C_8H_{17}$, A=single bond, i=1, h=2, X=H, Z=$CF_3$, k=5, l=1, n=2]

6-Ethoxy-1-trifluoromethylhexyl 4'-(4-octylphenylmethoxy)biphenyl-4-carboxylate was produced as in Example 8 except using p-octylbenzyl alcohol instead of p-octyloxybenzyl alcohol.

Figure 12:
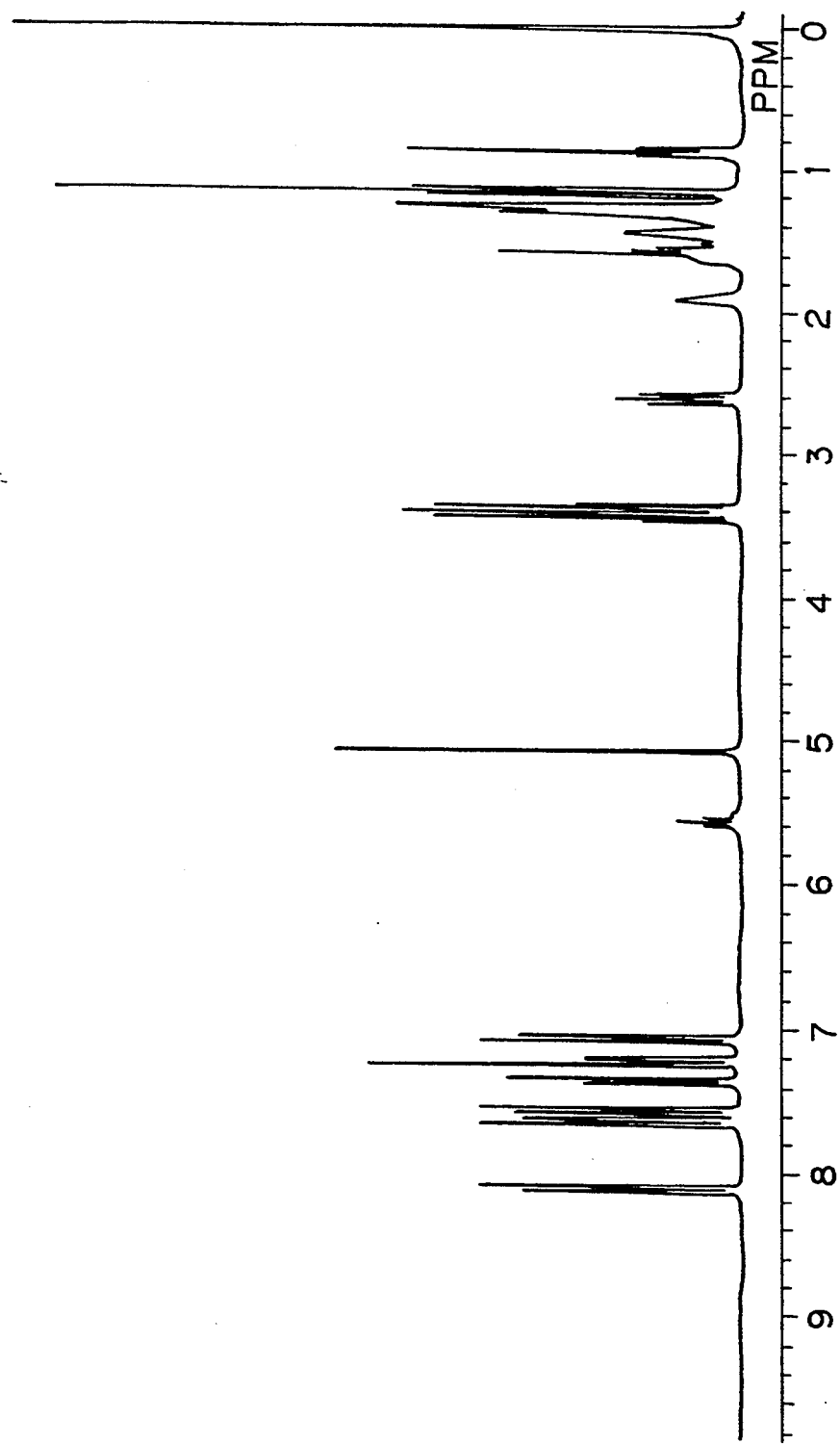
FIG. 12 is an NMR spectrum of the liquid crystal compound obtained in Example 10.

An NMR spectrum of the above compound is shown in FIG. 12.

Phase transition temperatures of the compound were measured as in Example 8 and determined as follows.

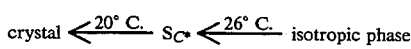

As is apparent from the phase transition temperatures, the compound was found to have a ferroelectric phase near room temperature.

EXAMPLE 11

Production of 1-methylpentyl 4-(4'-octyloxybiphenyl-4-yl-methoxy)benzoate

[In formula (1-b), R=n-$C_8H_{17}$, A=O, i=2, h=1, X=H, Z=$CH_3$, k=0, l=0, n=4]

(1) Production of 1-methylpentyl p-hydroxybenzoate

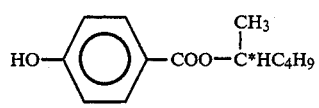

(1)

Thionyl chloride (25 ml) was added to 10 mmols of p-acetoxybenzoic acid, and the mixture was refluxed for 5 hours. Excess thionyl chloride was then completely removed. Thirty milliliters of toluene were added to the obtained chloride, and 7.1 mmols of R-(−)-2-hexanol and 3 ml of pyridine were added dropwise, followed by conducting the reaction overnight at room temperature. After the reaction, 50 ml of dichloromethane was added, and the organic layer was washed with a hydrochloric acid aqueous solution, a sodium hydroxide aqueous solution and water in this sequence. Subsequently, the organic layer was dried over anhydrous sodium sulfate, and the solvent was removed. The obtained composition was purified by silica gel column chromatography to obtain 1-methylpentyl p-acetoxybenzoate in a yield of 87%.

Said benzoate (4.7 mmols) was dissolved in 20 ml of ethanol, and 9.7 mmols of benzylamine were added. The mixture was stirred overnight. To the reaction mixture was added 50 ml of dichloromethane. The organic layer was washed with a hydrochloric acid aqueous solution and water in this sequence. Subsequently, the organic layer was dried over anhydrous sodium sulfate, and the solvent was evaporated. The obtained crude product was purified by silica gel column chromatography to afford 1-methylpentyl p-hydroxybenzoate in a yield of 100%.

(2) Production of 4′-octyloxy-4-hydroxymethylbiphenyl

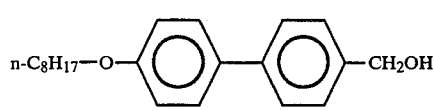

(2)

Lithium aluminium hydride (5.3 mmols) was suspended in 38 ml of tetrahydrofuran, and 3.1 mmols of 4′-octyloxybiphenyl-4-carboxylic acid were slowly added. After stirring at room temperature for 2 hours, the reaction mixture was charged into a large amount of water, and extracted with dichloromethane. After the extract was dried over anhydrous sodium sulfate, the solvent was evaporated to obtain a final product. Since said product showed 1 spot in thin layer chromatography, it was used in the next step without purification. The yield was 95%.

(3) Production of 1-methylpentyl 4-(4′-octyloxybiphenyl-4-yl-methoxy)benzoate

4′-Octyloxy-4-hydroxymethylbiphenyl (1.6 mmols) obtained in the above (2) was dissolved in 20 ml of tetrahydrofuran. The ester (1.5 mmols) obtained in the above (1) and 1.7 mmols of triphenylphosphine were added, and 2.4 mmols of diethyl azodicarboxylate were added dropwise. After the mixture was allowed to stand overnight at room temperature, tetrahydrofuran was evaporated, and the solid was purified with silica gel column chromatography. The yield was 72%.

Figure 13:
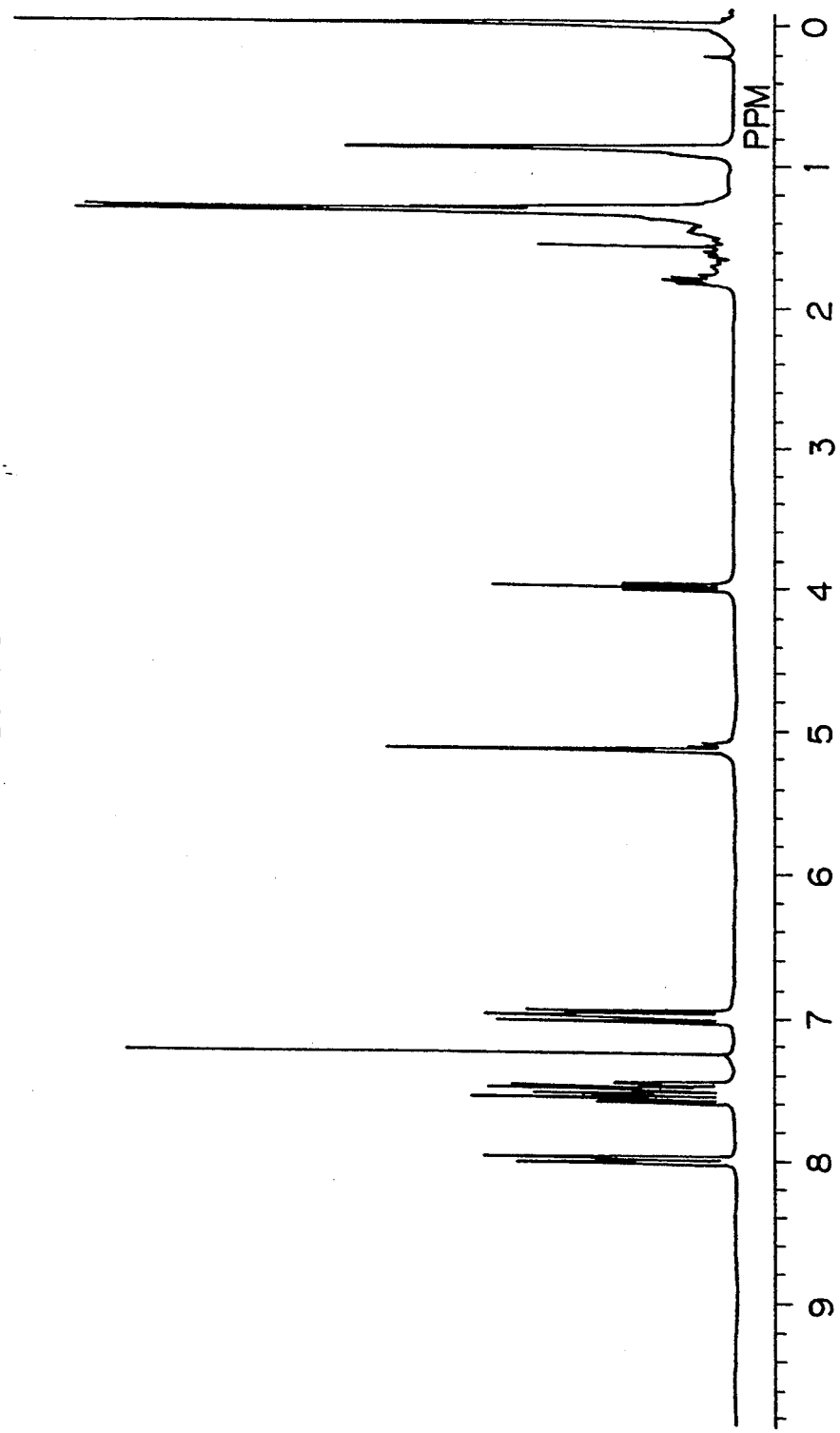
FIG. 13 is an NMR spectrum of the liquid crystal compound obtained in Example 11.

An NMR spectrum of the obtained compound is shown in FIG. 13. Identification of phases was conducted by observation of a texture and measurement with DSC.

Phase transition temperatures of the compound are as follows.

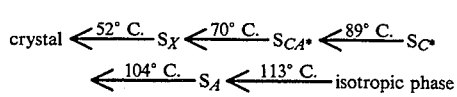

This compound had both the ferroelectric and anti-ferroelectric phases, but their temperatures were in a narrow range.

EXAMPLES 12, 13 and 14

Compounds having the same structure as in Example 10 were produced except using 4-acetoxy-3-fluorobenzoic acid instead of p-acetoxybenzoic acid and R-(+)-7-ethoxy-1,1,1-trifluoro-2-heptanol, S-(+)-3-nonanol and R-(−)-2-hexanol as optically active alcohols.

Figure 14:
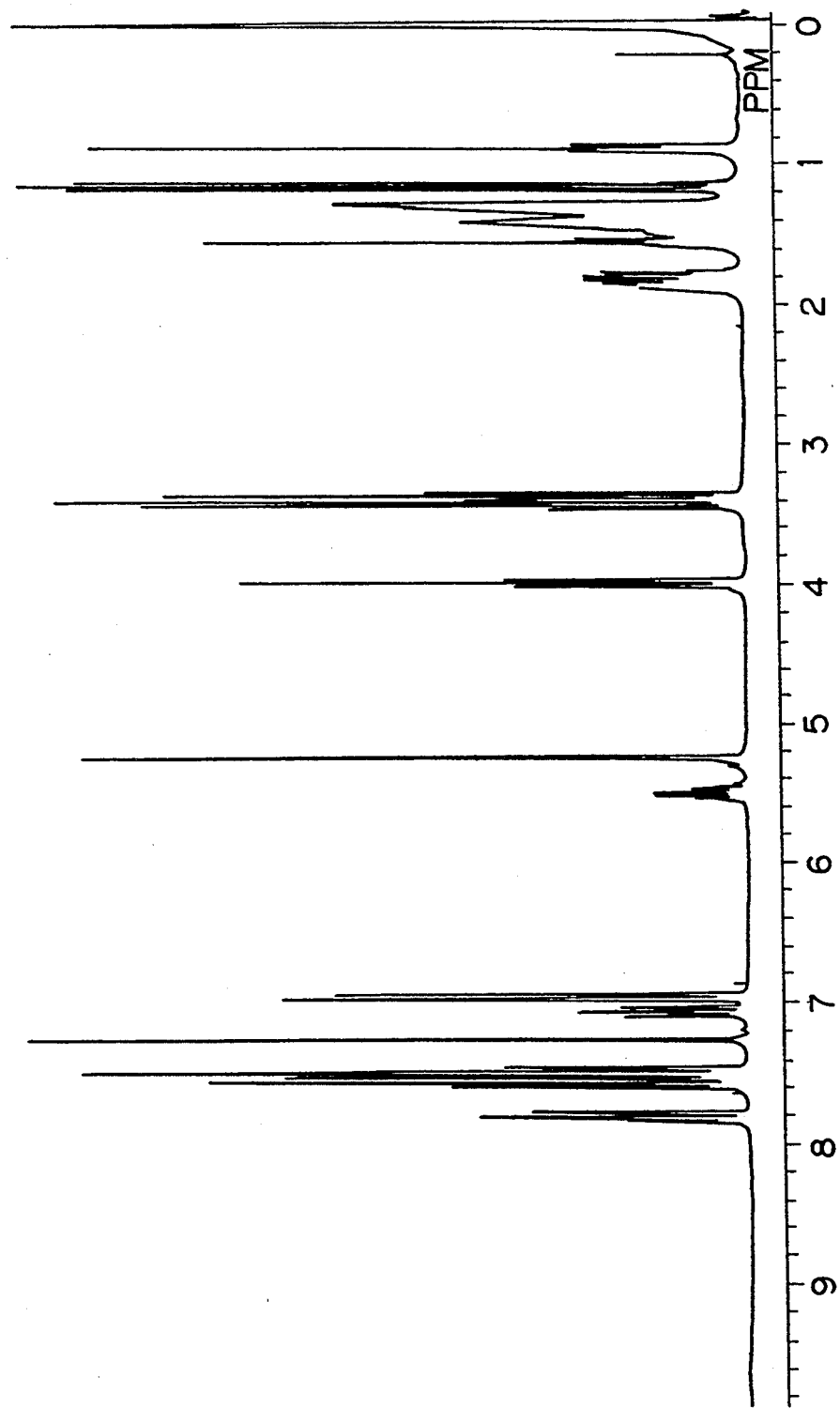
FIG. 14 is an NMR spectrum of the liquid crystal compound obtained in Example 12.
Figure 15:
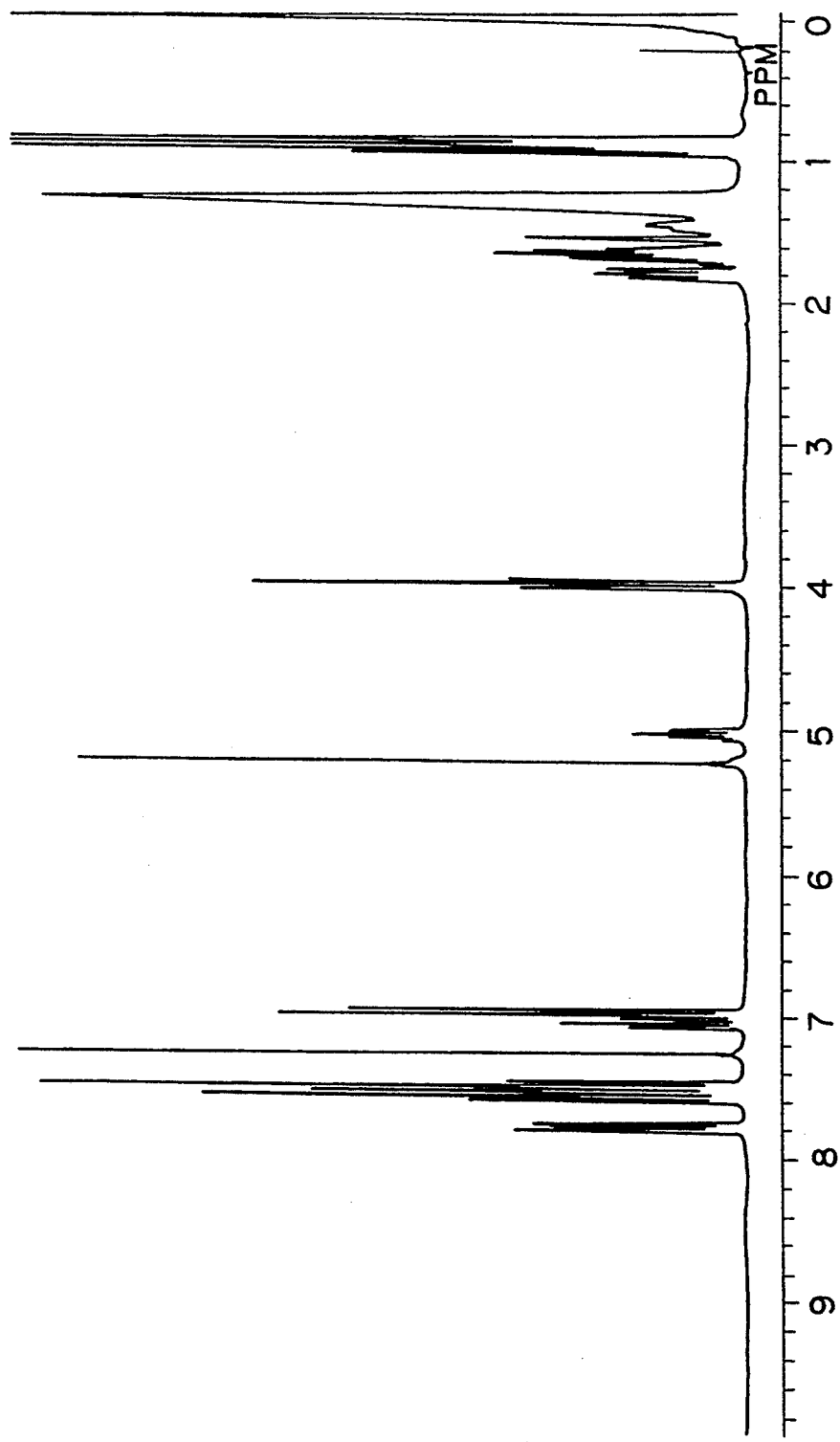
FIG. 15 is an NMR spectrum of the liquid crystal compound obtained in Example 13.
Figure 16:
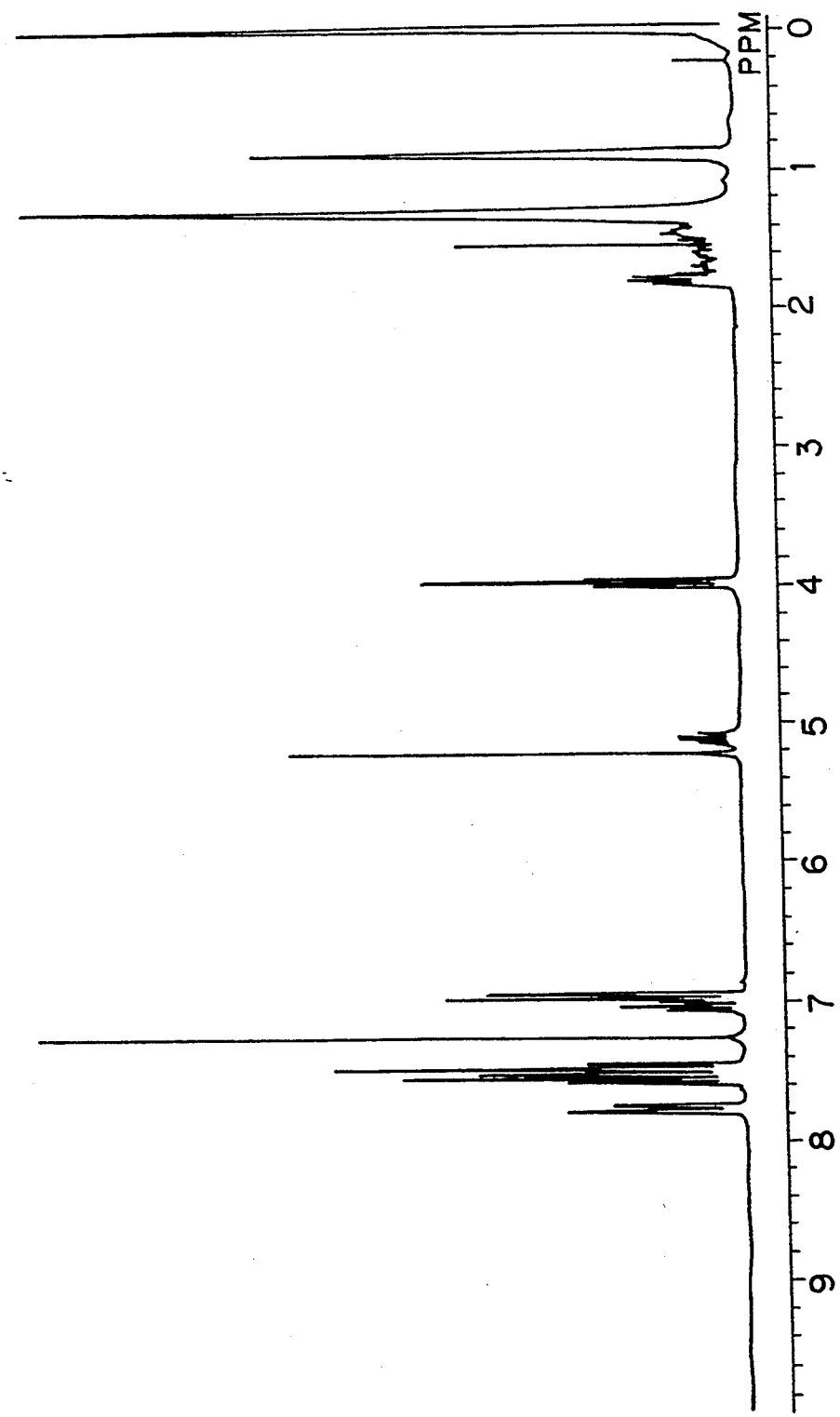
FIG. 16 is an NMR spectrum of the liquid crystal compound obtained in Example 14.

NMR sectra of these compounds are shown in FIGS. 14, 15 and 16.

Identification of phases was conducted by observation of a texture and measurement with DSC.

Phase transition temperatures of the compounds are shown in Table 3.

TABLE 3

| Phase transition temperatures of $C_8H_{17}-O-Ph-Ph-CH_2O-Ph(F)-COO-R^*$ |
|---|
| Example No. and −R*     Phase transition temperature |
| −C*H(CF$_3$)(CH$_2$)$_5$OC$_2$H$_5$     crystal ⇐ −8°C ⇒ S$_{CA*}$ ⇐ 21°C ⇒ S$_{C*}$ ⇐ 29°C ⇒ S$_A$ ⇐ 52°C ⇒ isotropic phase |
| −C*H(C$_2$H$_5$)C$_6$H$_{13}$     crystal ⇐ 12°C ⇒ S$_{C*}$ ⇐ 31°C ⇒ S$_A$ ⇐ 60°C ⇒ isotropic phase |
| −C*H(CH$_3$)C$_4$H$_9$     crystal ⇐ 24°C ⇒ S$_X$ ⇐ 35°C ⇒ S$_{CA*}$ ⇐ 55°C ⇒ S$_{C*}$ ⇐ 75°C ⇒ S$_A$ ⇐ 87°C ⇒ isotropic phase |

In the above table, S$_A$ is a smectic A phase.

As is clear from the above results, the anti-ferroelectric phase was found in the compounds of Examples 12 and 14, and the ferroelectric phase in the compounds of Examples 12, 13 and 14.

By the way, the ferroelectric phase was present in the antiferroelectric phase of the compound in Example 14, and said antiferroelectric phase was unstable.

Response speeds of the compound in Example 12 were measured at 11° C. as in Example 2. As a result, the response speed from the antiferroelectric phase to the ferroelectric phase was 530 microseconds, and that from the ferroelectric phase to the antiferroelectric phase was 650 microseconds; they were thus high response speeds.

EXAMPLE 15

Production of 6-ethoxy-1-trifluoromethylhexyl 4-(4'-octyloxybiphenyl-4-ylmethoxy)benzoate

[In formula (1-b), R=n-$C_8H_{17}$, A=O, i=2, h=1, X=H, Z=$CF_3$, k=5, l=1, n=2]

6-Ethoxy-1-trifluoromethylhexyl 4-(4'-octyloxybiphenyl-4-ylmethoxy)benzoate was produced as in Example 10 except using R-(+)-7-ethoxy-1,1,1-trifluoro-2-heptanol instead of R-(−)-2-hexanol in Example 14.

Figure 17:
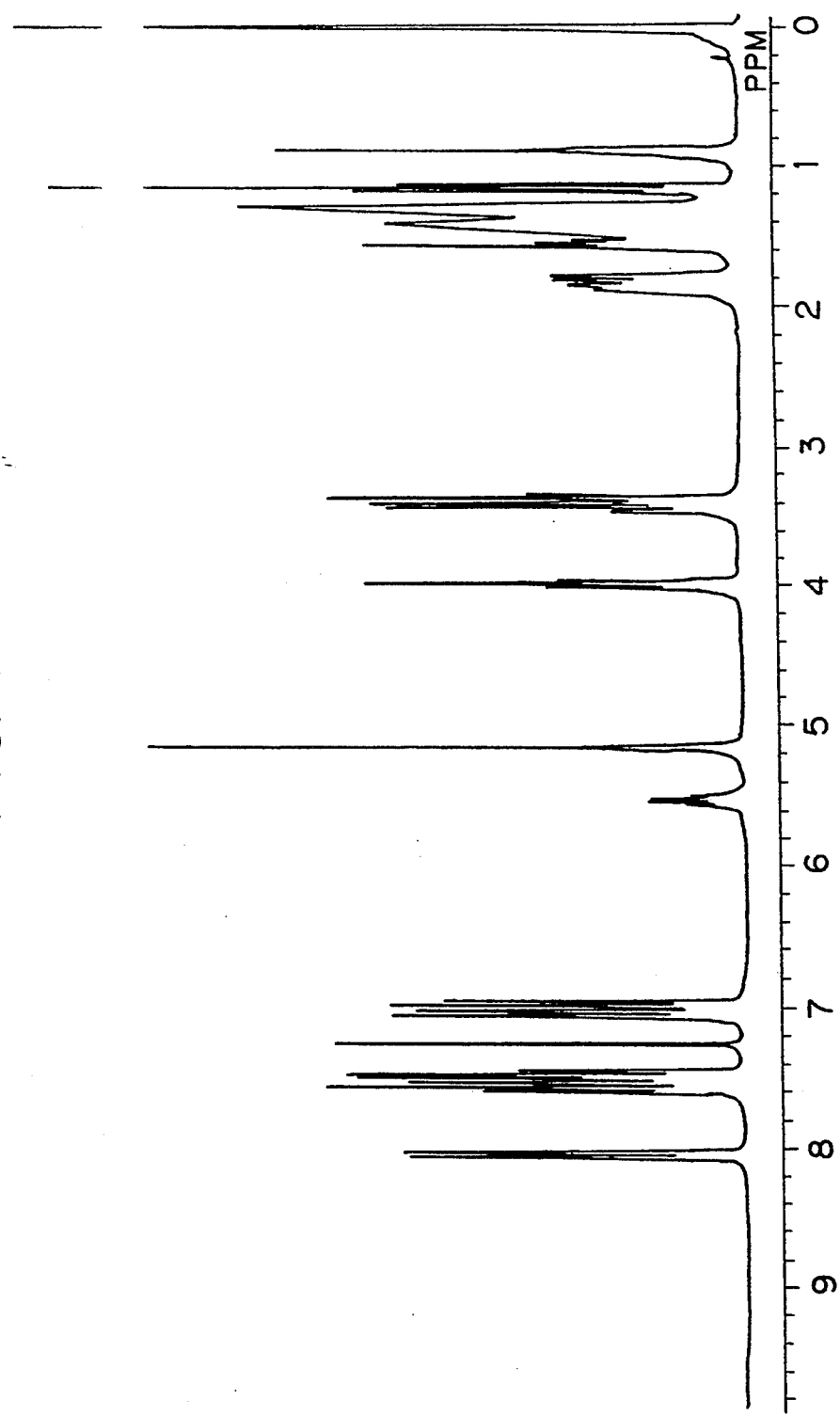
FIG. 17 is an NMR spectrum of the liquid crystal compound obtained in Example 15.

An NMR spectrum of this compound is shown in FIG. 17.

Identification of phases was conducted by observation of a texture and measurement with DSC.

Phase transition temperatures of the compound are as follows.

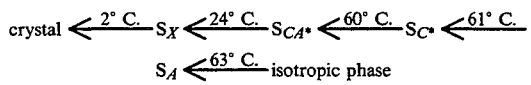

This compound had both the antiferroelectric and ferroelectric phases, and the antiferroelectric phase was observed in a wide temperature range including room temperature. Response speeds were measured as in Example 2, and it was found that at 48° C., the response speed from the antiferroelectric phase to the ferroelectric phase was 520 microseconds and that from the ferroelectric phase to the antiferroelectric phase was 430 microseconds.

EXAMPLE 16

Production of 3-fluoro-4-(1-methylnonyloxycarbonylphenyl) 4'-octyloxybiphenyl-4-carboxylate

[In formula (I-c), R=n-$C_8H_{17}$, W=$CH_3$, p=0, q=0, r=8]

1) Production of 4-(4'-n-octyloxy)biphenylcarboxylic acid (1)

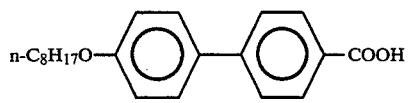

4-(4'-Hydroxy)biphenylcarboxylic acid (10.5 g), 14.0 g of n-octyl bromide, and 6.5 g of potassium hydroxide were added to a mixed solution of 1,500 ml of ethanol and 20 ml of water, and they were reacted under reflux for 10 hours. Further, 500 ml of water was added, and stirring was conducted for 3 hours. After the reaction was over, the reaction mixture was acidified with conc. hydrochloric acid, and 500 ml of the solvent was evaporated, followed by cooling the residue to room temperature. There resulted a white solid. The solid was fully washed with water, and recrystallized with chloroform to obtain 12.0 g of a final product (1) as a white crystal.

2) Production of 4-acetoxy-2-fluorobenzoic acid (2)

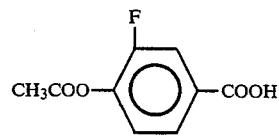

Four grams of 2-fluoro-4-hydroxybenzoic acid and 8 g of anhydrous acetic acid were taken in a two-necked flask and mixed. Five drops of sulfuric acid were added under ice cooling. After heat generation stopped, heating was conducted at 80° C. for 30 minutes. Subsequently, the reaction mixture was charged in cold water, and the precipitated crystals were filtered, then vacuum-dried and used in the next step. The yielded amount was 4.2 g.

3) Production of 4-acetoxy-2-fluoro-1-(1-methylnonyloxycarbonyl)benzene (3)

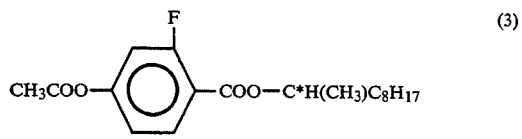

4-Acetoxy-2-fluorobenzoic acid (1.2 g) was added to 20 ml of thionyl chloride, and they were reacted under reflux for 5 hours. Then, excess thionyl chloride was evaporated, and a mixture of 3 ml of pyridine, 20 ml of toluene and 0.6 g of R-(−)-2-decanol was added dropwise. After the dropwise addition, stirring was conducted at room temperature for 24 hours. The reaction mixture was diluted with 50 ml of dichloromethane, and the organic layer was washed with dilute hydrochloric acid, a 1N sodium hydroxide aqueous solution and water in this sequence, and dried over sodium sulfate. The solvent was evaporated, and a crude final product was purified by silica gel column chromatography using a hexane/ethyl acetate solvent mixture to obtain 1.3 g of a final product (3).

4) Production of 2-fluoro-4-hydroxy-1-(1-methylnonyloxycarbonyl)benzene (4)

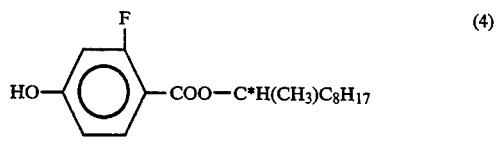

The above compound (3) (1.3 g) was dissolved in 30 ml of ethanol, and 0.8 g of benzylamine was added dropwise. Further, stirring was effected at room temperature for 24 hours. The reaction mixture was diluted with 50 ml of dichloromethane, washed with dilute hydrochloric acid and water in this sequence, and dried over sodium sulfate. After the solvent was evaporated, the solid was purified by silica gel column chromatography to afford 1.0 g of a final product (4).

5) Production of 3-fluoro-4-(1-methylnonyloxycarbonyl)phenyl 4'-n-octyloxybiphenyl-4-carboxylate (5)

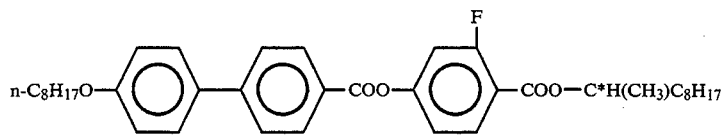

(5)

Ten milliliters of thionyl chloride were added to 0.9 g of the compound (1), and the mixture was refluxed for 5 hours. After excess thionyl chloride was evaporated, 2 ml of pyridine and 15 ml of toluene were added, and 0.6 g of the compound (4) was added dropwise, followed by reacting them at room temperature for 24 hours. After the reaction was over, the reaction mixture was diluted with 50 ml of dichloromethane. The organic layer was washed with dilute hydrochloric acid, a 1N sodium carbonate aqueous solution and water in this sequence, and dried over sodium sulfate. After the solvent was evaporated, the solid was purified by silica gel chromatography to afford 1.1 g of a final product (5).

Figure 18:
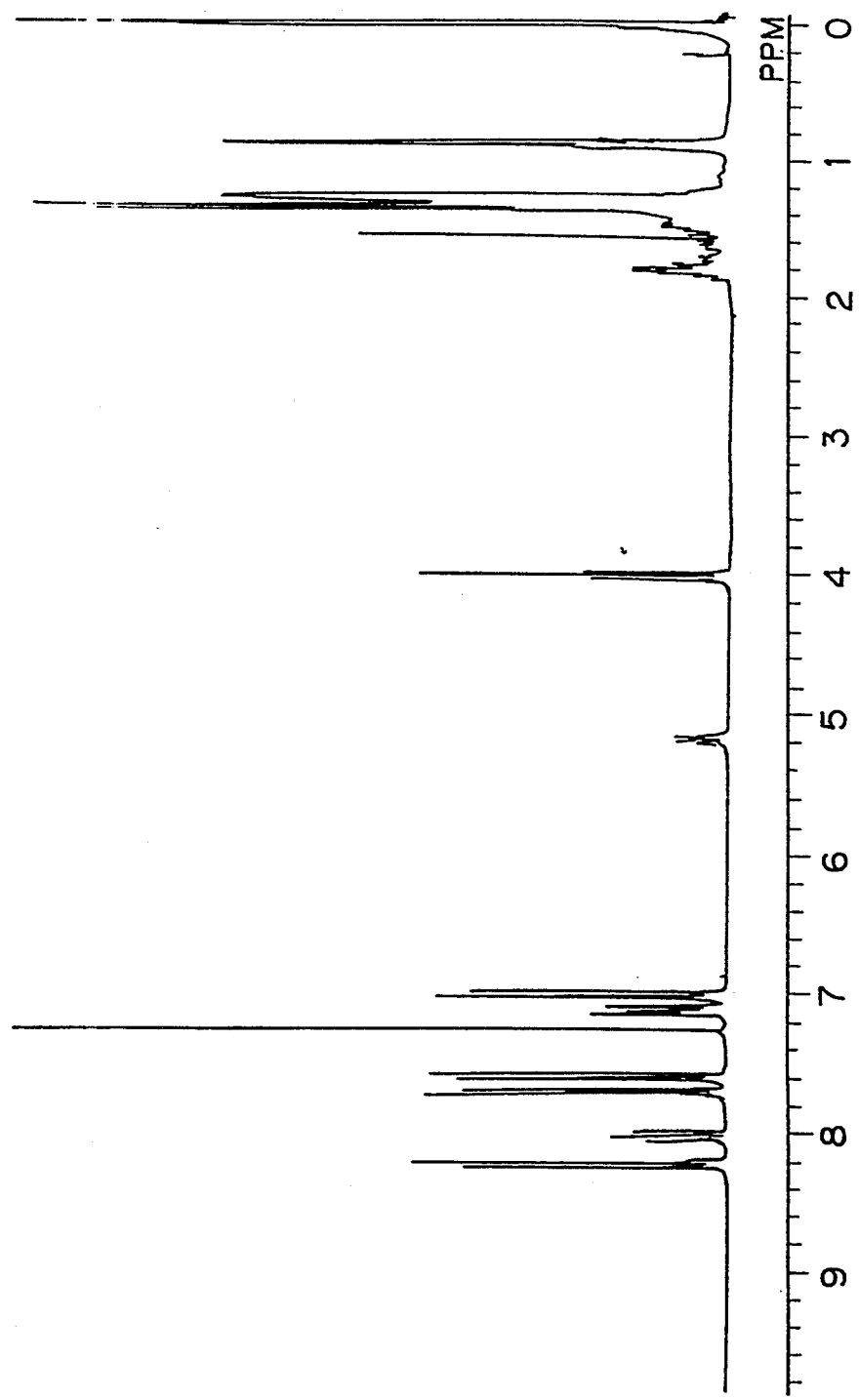
FIG. 18 is an NMR spectrum of the liquid crystal compound obtained in Example 16.

An NMR spectrum of the final product (5) is shown in FIG. 18.

Identification of phases was conducted by observation of a texture and measurement with DSC. A melting point was measured with DSC and found to be 36° C.

Phase transition temperatures of the liquid crystal compound (5) are as follows. An antiferroelectric phase was found in this compound.

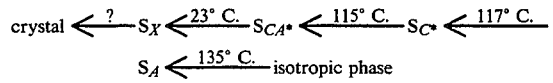

Figure 19:
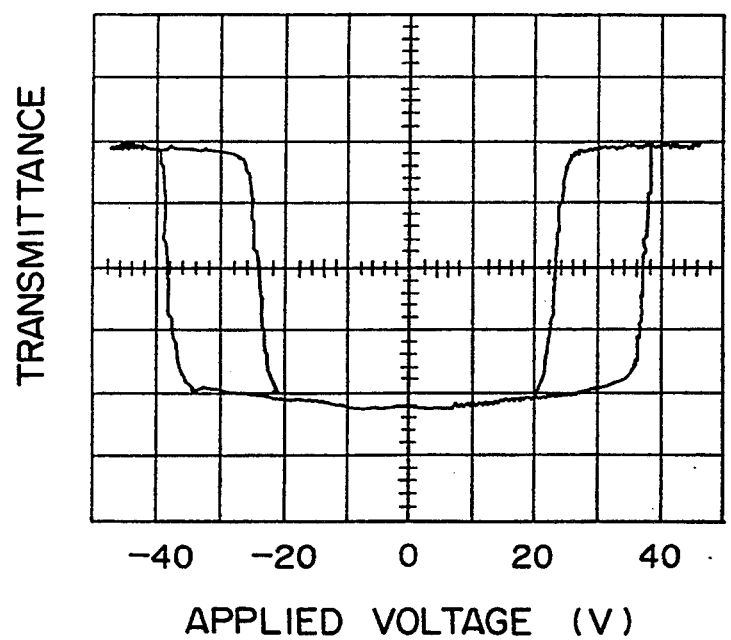
FIG. 19 is an optical response hysteresis of the liquid crystal compound obtained in Example 16.

6) Optical response was measured as in (6) of Example 1. As a result, a double hysteresis peculiar to the antiferroelectric phase was observed in a temperature region of from 115° C. to 25° C. An optical response hysteresis at 40° C. of the liquid crystal compound (5) is shown in FIG. 19.

Thus, the antiferroelectric liquid crystal compound (5) obtained in Example 16 had a low melting point, and part thereof was in a supercooled state. However, said compound showed antiferroelectricity in a wide temperature range including room temperature.

COMPARATIVE EXAMPLE 2

Production of 4-(1-methylnonyloxycarbonyl) phenyl 4'-octyloxybiphenyl-4-carboxylate 4-(1-Methylnonyloxycarbonyl)phenyl 4'-octyloxybiphenyl-4-carboxylate was produced as in Example 16 except using 4-acetoxybenzoic acid instead of 4-acetoxy-2-fluorobenzoic acid.

Figure 20:
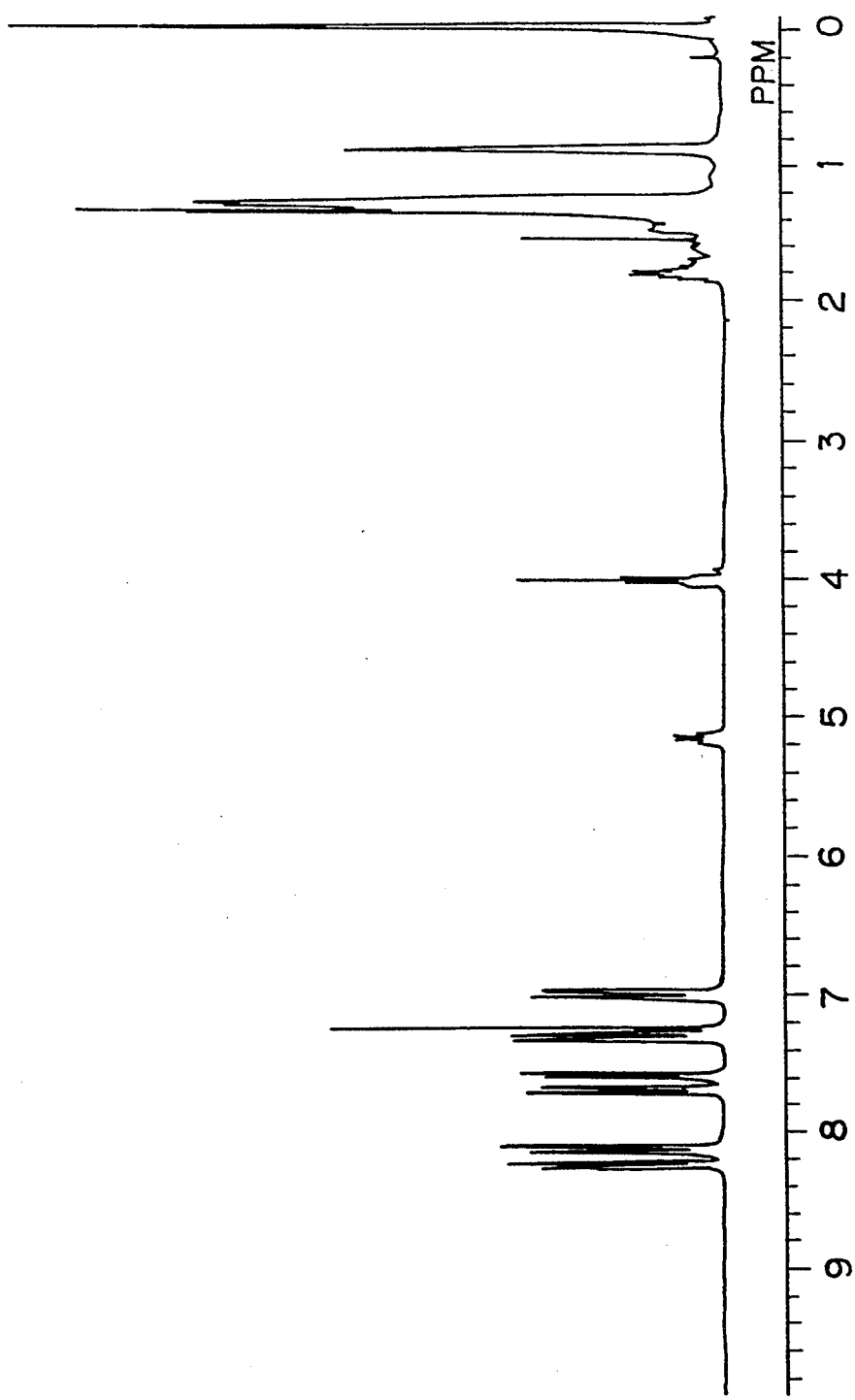
FIG. 20 is an NMR spectrum of the liquid crystal compound obtained in Comparative Example 2.

An NMR spectrum of the compound is shown in FIG. 20.

Identification of phases was conducted by observation of a texture and measurement with DSC. A melting point was measured with DSC.

Phase transition temperatures of the compound are as follows. An antiferroelectric phase was observed in said compound, and its melting point was 67° C.

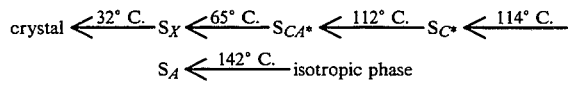

EXAMPLE 17

Production of 3-fluoro-4-(1-methylnonyloxycarbonyl)phenyl 4'-heptyloxybiphenyl-4-carboxylate

[In formula (I-c), R=n-$C_7H_{15}$, W=$CH_3$, p=0, q=0, r=8]

3-Fluoro-4-(1-methylnonyloxycarbonyl)phenyl 4'-heptyloxybiphenyl-4-carboxylate was produced as in Example 16 except using n-heptyl bromide instead of n-octyl bromide.

Figure 21:
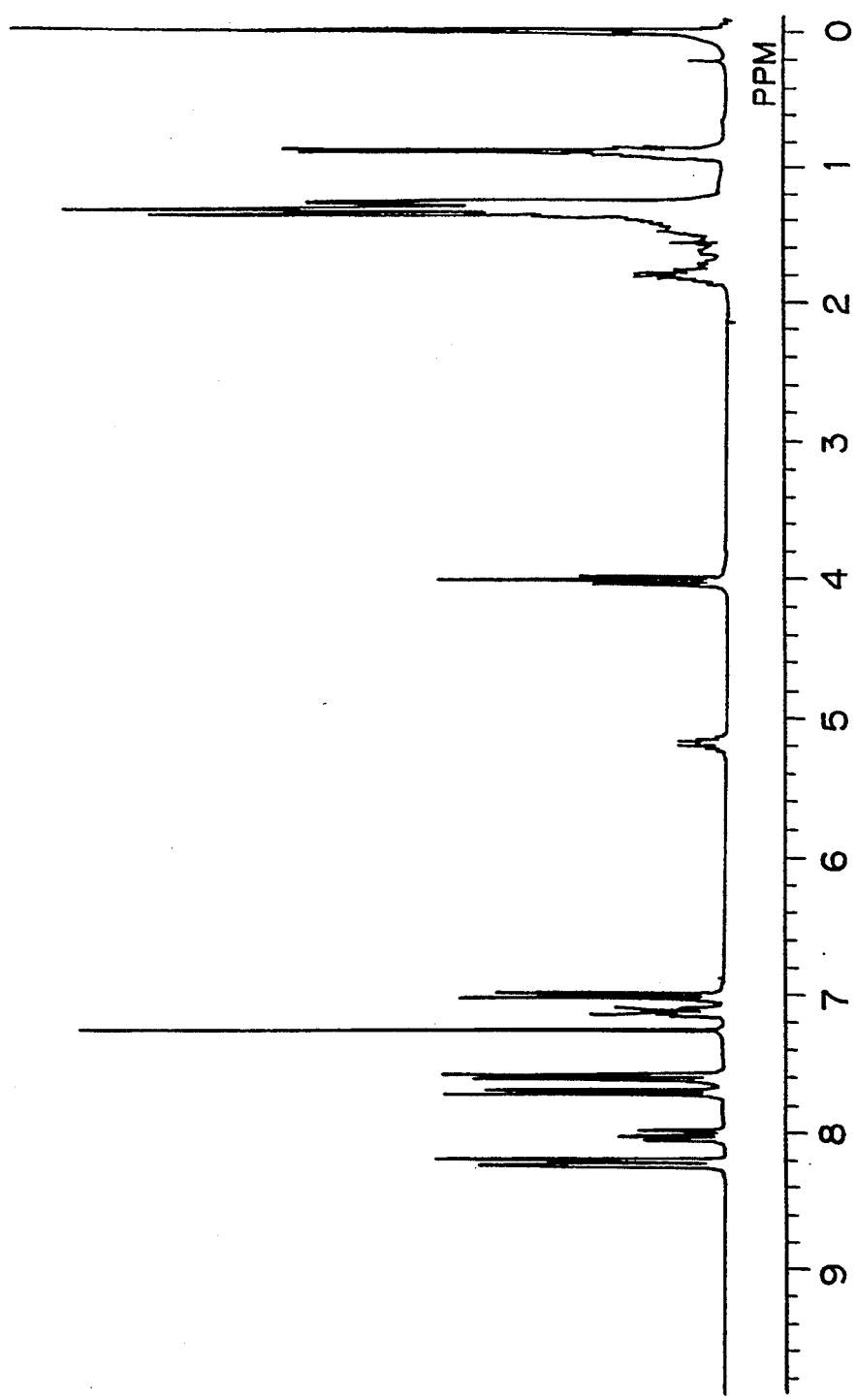
FIG. 21 is an NMR spectrum of the liquid crystal compound obtained in Example 17.

An NMR spectrum of a final product is shown in FIG. 21.

Identification of phases was conducted by observation of a texture and measurement with DSC. A melting point was measured with DSC.

Phase transition temperatures of the liquid crystal compound are as follows. An antiferroelectric phase was observed in this compound, and its melting point was 70° C.

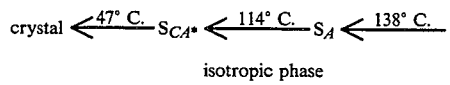

This compound had a higher melting point than that in Example 14 because R was $C_7H_{15}$, but the temperature range of the antiferroelectric phase was enlarged.

EXAMPLE 18

Production of 3-fluoro-4-(1-trifluoromethyl-6-ethoxyhexyloxycarbonyl)phenyl 4'-octyloxybiphenyl-4-carboxylate

[In formula (I-c), R=n-$C_8H_{17}$, W=$CF_3$, p=5, q=1, r=2]

3-Fluoro-4-(1-trifluoromethyl-6-ethoxyhexyloxycarbonyl)phenyl 4'-octyloxybiphenyl-4-carboxylate was produced as in Example 16 except using R-(−)-1,1,1-trifluoro-7-ethoxy-2-heptanol instead of R-(−)-2-decanol.

Figure 22:
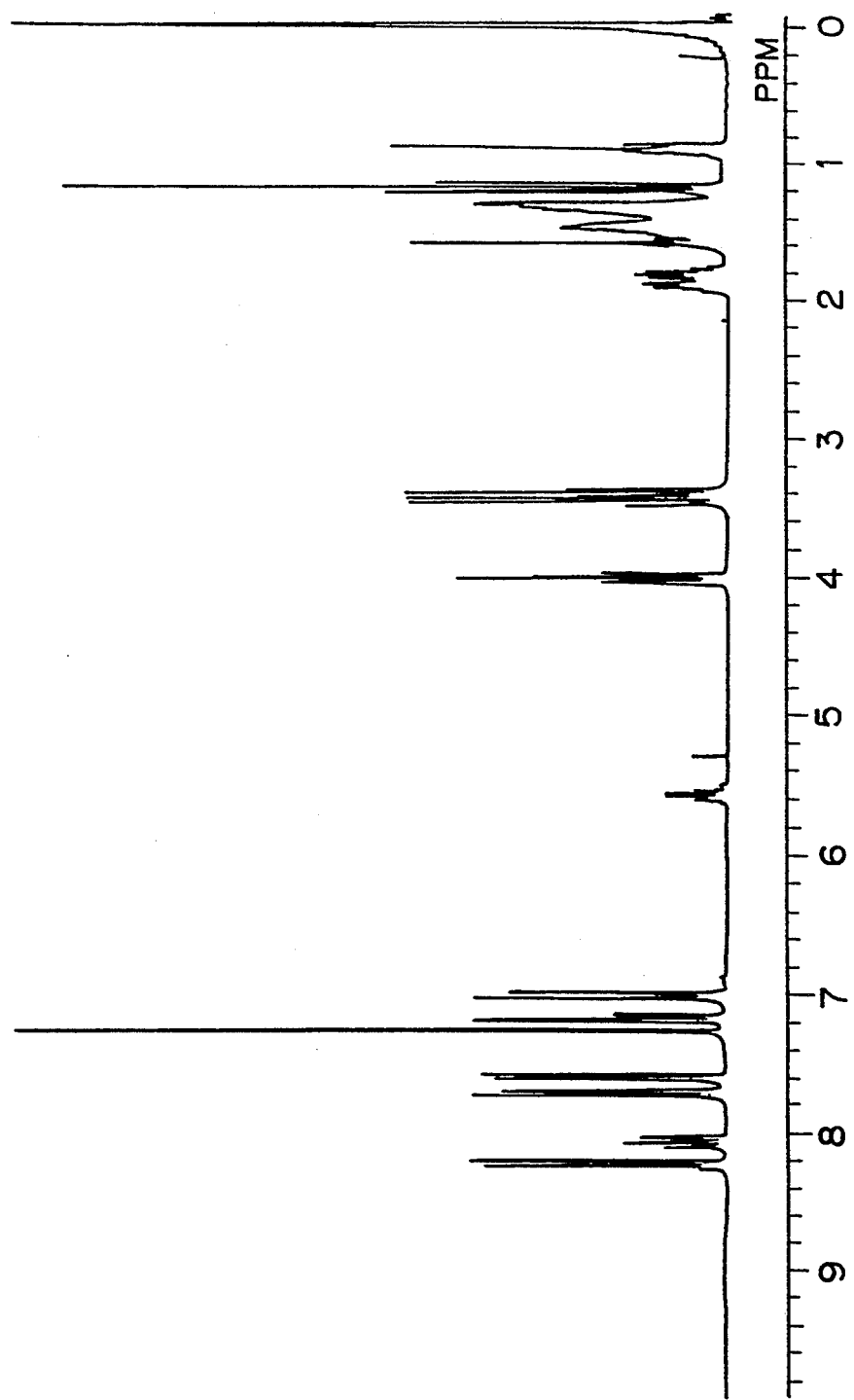
FIG. 22 is an NMR spectrum of the liquid crystal compound obtained in Example 18.

An NMR sectrum of the resulting liquid crystal compound is shown in FIG. 22.

Identification of phases was conducted by observation of a texture and measurement with DSC. A melting point was measured with DSC.

Phase transition temperatures of the liquid crystal compound are as follows. An antiferroelectric phase was observed in the compound, and its melting point was 82° C.

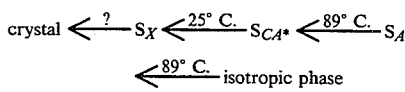

Although part of the antiferroelectric phase of this liquid crystal compound was in a supercooled state, the antiferroelectric phase was in a wide temperature range including room temperature.

COMPARATIVE EXAMPLE 3

Production of 4-(1-trifluoromethyl-6-ethoxy hexyloxycarbonyl)phenyl 4'-octyloxybiphenyl-4-carboxylate In the same way as in Example 18, 4-(1-trifluoromethyl-7-ethoxyhexyloxycarbonyl)phenyl 4'-octyloxybiphenyl-4-carboxylate was produced except using 4-acetoxybenzoic acid instead of 4-acetoxy-2-fluorobenzoic acid.

Figure 23:
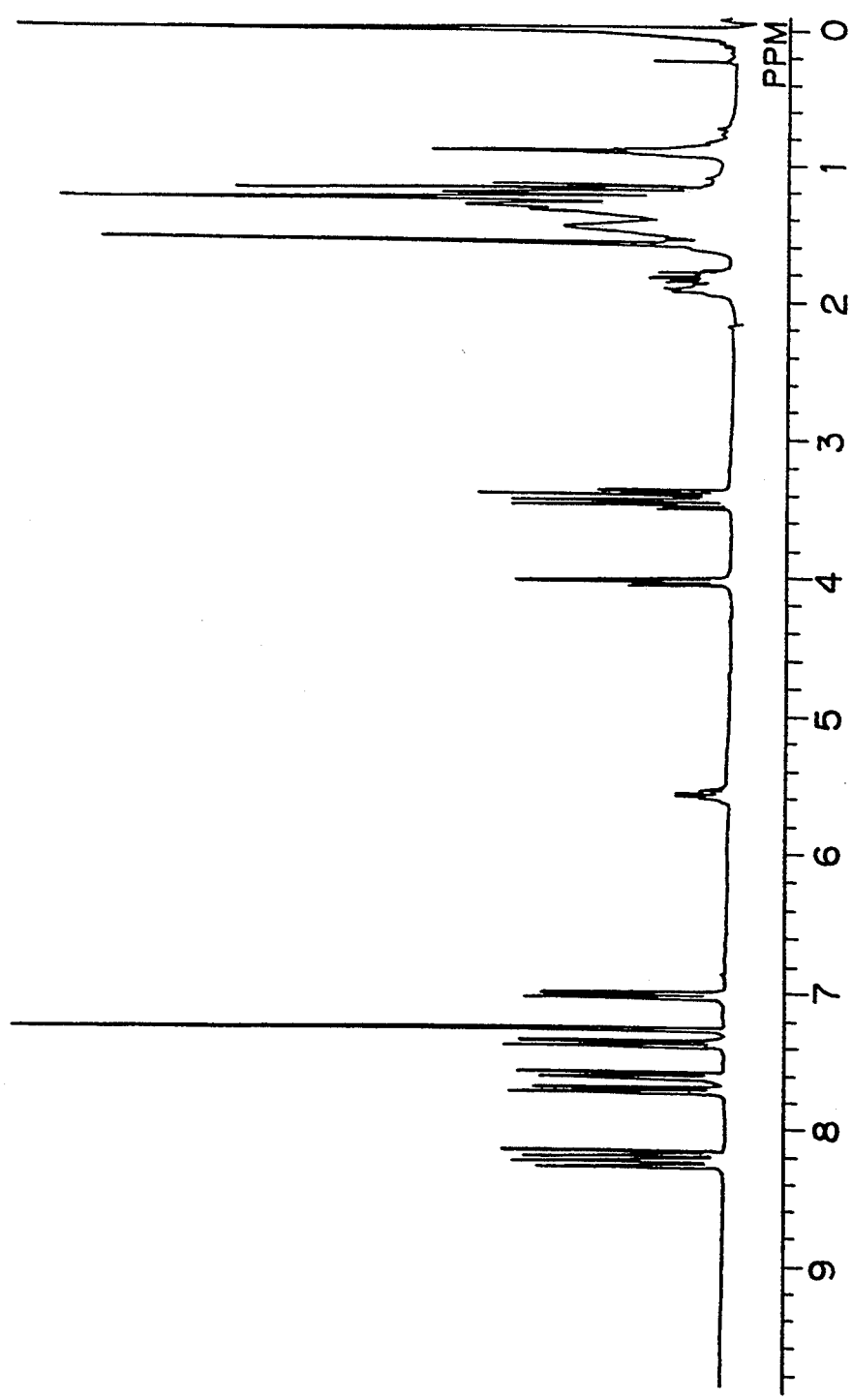
FIG. 23 is an NMR spectrum of the liquid crystal compound obtained in Comparative Example 3.

An NMR spectrum of the resulting liquid crystal compound is shown in FIG. 23.

Identification of phases was conducted by observation of a texture and measurement with DSC. A melting point was measured with DSC.

Phase transition temperatures of the compound are as follows. An antiferroelectric phase was observed in this compound, and its melting point was 59° C.

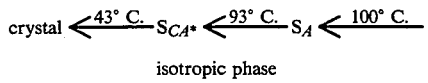

EXAMPLE 19

Production of 3-fluoro-4-(1-trifluoromethyl-8-ethoxyheptyloxycarbonyl)phenyl 4'-octyloxybiphenyl- 4-carboxylate

[In formula (1-c), R=n-$C_8H_{17}$, W=$CH_3$, p=7, q=1, r=2]

In the same say as in Example 16, 3-fluoro-4-(1-trifluoromethyl-8-ethoxyheptyloxycarbonyl)phenyl 4'-octyloxybiphenyl-4-carboxylate was produced except using R-(−)-1,1,1-trifluoromethyl-9-ethoxy-2-nonanol instead of R-(−)-1,1,1-trifluoromethyl-7-ethoxy-2-heptanol.

Figure 24:
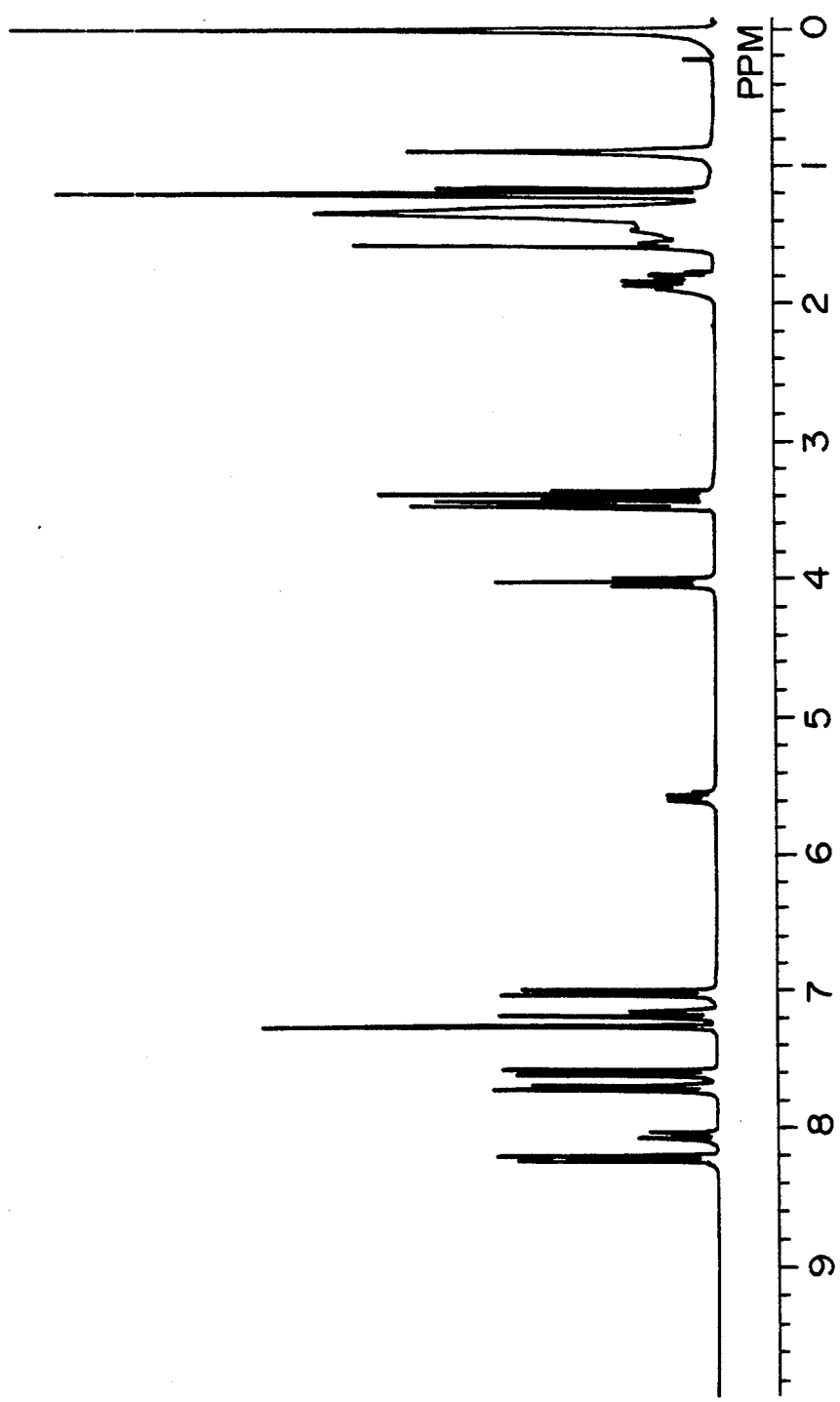
FIG. 24 is an NMR spectrum of the liquid crystal compound obtained in Example 19.

An NMR spectrum of the resulting compound is shown in FIG. 24.

Identification of phases was conducted by observation of a texture and measurement with DSC. A melting point was measured with DSC.

Phase transition temperatures of the liquid crystal compound are as follows. An antiferroelectric phase was observed in this compound, and its melting point was 86° C.

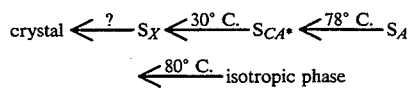

What we claim is:

1. A liquid crystal compound which is a compound represented by (1) formula (I-a)

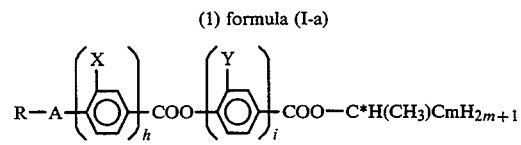

wherein C* denotes an asymmetric carbon atom, and wherein the compound is a member selected from the group consisting of compounds in which the substituents have the following values:

(a) R=n-$C_8H_{17}$, A=O, h=2, i=1, X=H, Y=F, m=4, 6 or 8
(b) R=n-$C_{11}H_{23}$, A=O, h=2, i=1, X=H, Y=F, m=6
(c) R=n-$C_{14}H_{29}$, A=O, h=2, i=1, X=H, Y=F, m=6 or (2) formula (I-b)

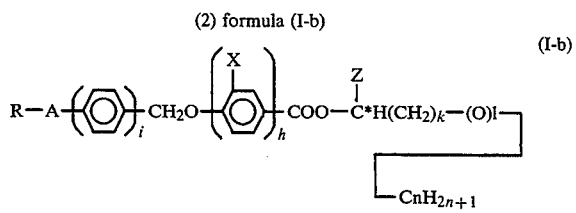

wherein C* denotes an asymmetric carbon atom, and wherein the compound is a member selected from the group consisting of compounds in which the substituents have the following values:

(a) R=n-$C_8H_7$, A=O, i=1, h=2, X=H, Z=$CF_3$, k=5 or 7, l=1, n=2
(b) R=n-$C_8H_{17}$, A=O, i=2, h=1, X=H or F, Z=$CF_3$, k=5, l=1, n=2
(c) R=n-$C_8H_{17}$, A=O, i=2, h=1, X=H or F, Z=$CH_3$, k=0, l=0, n=4 or (3) formula (I-c)

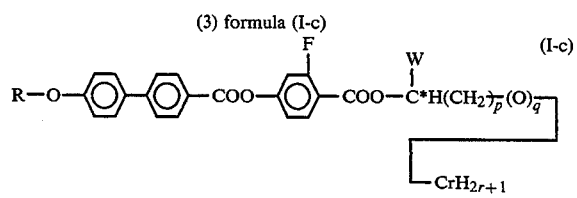

wherein C* denotes an asymmetric carbon atom, and wherein the compound is a member selected from the group consisting of compounds in which the substituents have the following values:

(a) R=n-$C_7H_{15}$, W=$CH_3$, p=0, q=0, r=8
(b) R=n-$C_8H_{17}$, W=$CH_3$, p=0, q=0, r=8
(c) R=n-$C_8H_{17}$, W=$CF_3$, p=5 or 7, q=1, r=2.

2. A liquid crystal display device using the liquid crystal compound of claim 1.

3. An antiferroelectric liquid crystal compound which is a compound represented by Formula (I-a)

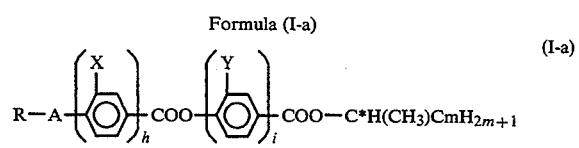

wherein C* denotes an asymmetric carbon atom, and wherein the compound is a member selected from the group consisting of compounds in which the substituents have the following values:

(a) R=n-$C_8H_{17}$, A—O, h=2, i=1, X=H, Y=F, m=4, 6 or 8
(b) R=n-$C_{11}H_{23}$, A=O, h=2, i=1, X=H, Y=F, m=6
(c) R=n-$C_{14}H_{29}$, A=O, h=2, i=1, X=H, Y=F, m=6.

4. A liquid crystal display device using the liquid crystal compound of claim 3.

5. An antiferroelectric liquid crystal compound which is a compound represented by formula (I-b)

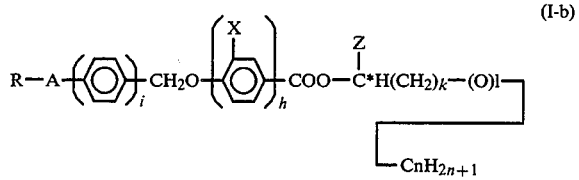

wherein C* denotes an asymmetric carbon atom, and wherein the compound is a member selected from the group consisting of compounds in which the substituents have the following values:

(a) R=n-$C_8H_{17}$, A=0, i=1, h=2, X=H, Z=$CF_3$, k=5 or 7, l=1, n=2

(b) R=n-$C_8H_{17}$, A=0, i=2, h=1, X=H or F, Z=$CF_3$, k=5, l=1, n=2

(c) R=n-$C_8H_{17}$, A=0, i=2, h=1, X=H or F, Z=$CH_3$, k=0, l=0, n=4.

6. A liquid crystal display device using the liquid crystal compound of claim 5.

7. An antiferroelectric liquid crystal compound which is a compound represented by formula (I-c)

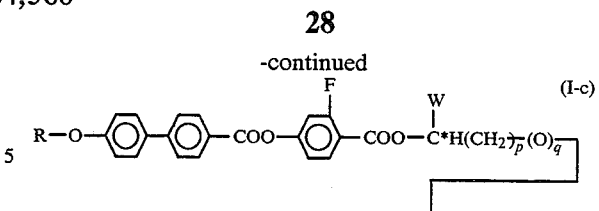

wherein C* denotes an asymmetric carbon atom, and wherein the compound is a member selected from the group consisting of compounds in which the substituents have the following values:

(a) R=n-$C_7H_{15}$, W=$CH_3$, p=0, q=0, r=8
(b) R=n-$C_8H_{17}$, W=$CH_3$, p=0, q=0, r=8
(c) R=n-$C_8H_{17}$, W=$CF_3$ p=5 or 7, q=1, r=2.

8. A liquid crystal display device using the liquid crystal compound of claim 7.

9. A liquid crystal compound which is a compound represented by formula (I-c)

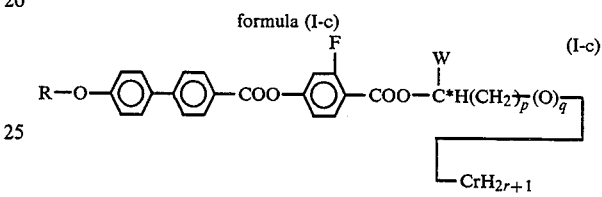

wherein R denotes a linear aliphatic alkyl group having 7 carbon atoms; W denotes $CF_3$; p is 5 to 8, q is 1 and r is 2; and C* denotes an asymmetric carbon atom.

10. The liquid crystal compound of claim 9 wherein p is 5.

11. The liquid crystal compound of claim 9 wherein p is 7.

12. A liquid crystal display device using the liquid crystal compound of claim 9.

* * * * *